(12) United States Patent
Conn et al.

(10) Patent No.: US 6,341,232 B1
(45) Date of Patent: Jan. 22, 2002

(54) METHODS OF PRODUCING COLLECTION ASSEMBLIES, LAMINATES, AND AUTOSENSOR ASSEMBLIES FOR USE IN TRANSDERMAL SAMPLING SYSTEMS

(75) Inventors: Thomas E. Conn, Palo Alto; Russell Ford, San Francisco; Pravin L. Soni, Sunnyvale; Michael J. Tierney, San Jose; Prema Vijayakumar, Fremont, all of CA (US)

(73) Assignee: Cygnus, Inc., Redwood City, CA (US)

( * ) Notice: Subject to any disclaimer, the term of this patent is extended or adjusted under 35 U.S.C. 154(b) by 0 days.

(21) Appl. No.: 09/810,917

(22) Filed: Mar. 16, 2001

Related U.S. Application Data

(63) Continuation of application No. 09/309,616, filed on May 11, 1999.
(60) Provisional application No. 60/085,345, filed on May 13, 1999.

(51) Int. Cl.[7] .............................. A61N 1/30; A61B 5/05
(52) U.S. Cl. .......................... 604/20; 604/501; 600/345
(58) Field of Search ............................ 604/20, 21, 500, 604/501, 504; 606/152, 153; 600/300, 309, 345–348, 362, 372, 365

(56) References Cited

U.S. PATENT DOCUMENTS

| | | | |
|---|---|---|---|
| 4,975,581 A | 12/1990 | Robinson et al. |
| 5,036,861 A | 8/1991 | Sembrowich et al. |
| 5,076,273 A | 12/1991 | Schoendorfer et al. |
| 5,086,229 A | 2/1992 | Rosenthal et al. |
| 5,139,023 A | 8/1992 | Stanley et al. |
| 5,140,985 A | 8/1992 | Schroeder et al. |
| 5,167,617 A | 12/1992 | Sibalis |
| 5,224,928 A | 7/1993 | Sibalis |
| 5,267,152 A | 11/1993 | Yang et al. |
| 5,279,543 A | 1/1994 | Glikfeld et al. |
| 5,362,307 A | 11/1994 | Guy et al. |
| 5,443,080 A | 8/1995 | D'Angelo et al. |
| 5,730,714 A | 3/1998 | Guy et al. |
| 5,735,273 A | 4/1998 | Kurnik et al. |
| 5,771,890 A | 6/1998 | Tamada |
| 5,827,183 A | 10/1998 | Kurnik et al. |
| 5,954,685 A | 9/1999 | Tierney |
| 5,989,409 A | 11/1999 | Kurnik et al. |
| 6,141,573 A | 10/2000 | Kurnik et al. |
| 6,144,869 A | 11/2000 | Berner et al. |

FOREIGN PATENT DOCUMENTS

| | | |
|---|---|---|
| EP | 0 625 360 A1 | 11/1994 |
| WO | WO 89/06555 | 7/1989 |
| WO | WO 95/02357 | 1/1995 |
| WO | WO 96/00109 | 1/1996 |
| WO | WO/96/00110 | 1/1996 |
| WO | WO/97/10356 | 3/1997 |
| WO | WO97/24059 | 7/1997 |

OTHER PUBLICATIONS

The Diabetes Control and Complications Trial Research, *New Engl. J. Med.* 329:977–1036 (1993).

*Primary Examiner*—Sharon Kennedy
(74) *Attorney, Agent, or Firm*—Barbara G. McClung; Robins & Pasternak LLP

(57) ABSTRACT

The invention relates generally to methods of producing consumable components of a device used for measuring the concentration of target chemical analytes present in a biological system. More particularly, the invention relates methods of producing collection assemblies, laminate structures, and autosensor assemblies, which are used in connection with a transdermal sampling device. In one aspect, the invention includes methods of producing autosensor assemblies which include laminate structures, electrode assemblies, and support trays. One important application of the invention involves methods of producing an autosensor assembly for use in a blood glucose monitoring device.

59 Claims, 16 Drawing Sheets

METHODS OF PRODUCING COLLECTION ASSEMBLIES, LAMINATES, AND AUTOSENSOR ASSEMBLIES FOR USE IN TRANSDERMAL SAMPLING SYSTEMS

CROSS-REFERENCE TO RELATED APPLICATION

This application is a continuation of U.S. patent application Ser. No. 09/309,616, filed May 11, 1999, now allowed, which claims priority to provisional patent application Ser. No. 60/085,345 filed May 13, 1998, from which applications priority is claimed pursuant to 35 U.S.C. § 120 and which are incorporated herein by referenced in their entireties.

TECHNICAL FIELD OF THE INVENTION

Novel laminate structures, collection assemblies, and autosensor assemblies for use in a sampling device are described. The invention relates generally to consumable components of a device used for continually or continuously measuring the concentration of target chemical analytes present in a biological system. The laminates, collection assemblies, and autosensor assemblies are used in a transdermal sampling device that is placed in operative contact with a skin or mucosal surface of a biological system to obtain a chemical signal associated with an analyte of interest.

BACKGROUND OF THE INVENTION

A number of diagnostic tests are routinely performed on humans to evaluate the amount or existence of substances present in blood or other body fluids. These diagnostic tests typically rely on physiological fluid samples removed from a subject, either using a syringe or by pricking the skin. One particular diagnostic test entails self-monitoring of blood glucose levels by diabetics.

Diabetes is a major health concern, and treatment of the more severe form of the condition, Type I (insulin-dependent) diabetes, requires one or more insulin injections per day. Insulin controls utilization of glucose or sugar in the blood and prevents hyperglycemia which, if left uncorrected, can lead to ketosis. On the other hand, improper administration of insulin therapy can result in hypoglycemic episodes, which can cause coma and death. Hyperglycemia in diabetics has been correlated with several long-term effects of diabetes, such as heart disease, atherosclerosis, blindness, stroke, hypertension and kidney failure.

The value of frequent monitoring of blood glucose as a means to avoid or at least minimize the complications of Type I diabetes is well established. Patients with Type II (non-insulin-dependent) diabetes can also benefit from blood glucose monitoring in the control of their condition by way of diet and exercise.

Conventional blood glucose monitoring methods generally require the drawing of a blood sample (e.g., by finger prick) for each test, and a determination of the glucose level using an instrument that reads glucose concentrations by electrochemical or colorimetric methods. Type I diabetics must obtain several finger prick blood glucose measurements each day in order to maintain tight glycemic control. However, the pain and inconvenience associated with this blood sampling, along with the fear of hypoglycemia, has led to poor patient compliance, despite strong evidence that tight control dramatically reduces long-term diabetic complications. In fact, these considerations can often lead to an abatement of the monitoring process by the diabetic. See, e.g., The Diabetes Control and Complications Trial Research Group (1993) *New Engl. J. Med.* 329:977–1036.

Recently, various methods for determining the concentration of blood analytes without drawing blood have been developed. For example, U.S. Pat. No. 5,267,152 to Yang et al. describes a noninvasive technique of measuring blood glucose concentration using near-IR radiation diffuse-reflection laser spectroscopy. Similar near-IR spectrometric devices are also described in U.S. Pat. No. 5,086,229 to Rosenthal et al. and U.S. Pat. No. 4,975,581 to Robinson et al.

U.S. Pat. Nos. 5,139,023 to Stanley et al., and 5,443,080 to D'Angelo et al. describe transdermal blood glucose monitoring devices that rely on a permeability enhancer (e.g., a bile salt) to facilitate transdermal movement of glucose along a concentration gradient established between interstitial fluid and a receiving medium. U.S. Pat. No. 5,036,861 to Sembrowich describes a passive glucose monitor that collects perspiration through a skin patch, where a cholinergic agent is used to stimulate perspiration secretion from the eccrine sweat gland. Similar perspiration collection devices are described in U.S. Pat. No. 5,076,273 to Schoendorfer and U.S. Pat. No. 5,140,985 to Schroeder.

In addition, U.S. Pat. No. 5,279,543 to Glikfeld et al. describes the use of iontophoresis to noninvasively sample a substance through skin into a receptacle on the skin surface. Glikfeld teaches that this sampling procedure can be coupled with a glucose-specific biosensor or glucose-specific electrodes in order to monitor blood glucose. Finally, International Publication No. WO 96/00110, published Jan. 4, 1996, describes an iontophoretic apparatus for transdermal monitoring of a target substance, wherein an iontophoretic electrode is used to move an analyte into a collection reservoir and a biosensor is used to detect the target analyte present in the reservoir. Finally, International Publication No. WO 96/00110 to Tamada describes an iontophoretic apparatus for transdermal monitoring of a target substance, where an iontophoretic electrode is used to move an analyte into a collection reservoir and a biosensor is used to detect the target analyte present in the reservoir.

SUMMARY OF THE INVENTION

The present invention relates generally to collection assembly, laminates and autosensor assemblies for use in a sampling device. More particularly, the present collection assembly, laminates and autosensor assemblies are used in a transdermal sampling device that is placed in operative contact with a skin or mucosal surface of the biological system to obtain a chemical signal associated with an analyte of interest. The sampling device transdermally extracts the analyte from the biological system using, for example, an iontophoretic sampling technique. The transdermal sampling device can be maintained in operative contact with the skin or mucosal surface of the biological system to provide, for example, continual or continuous analyte measurement.

The analyte can be any specific substance or component that one is desirous of detecting and/or measuring in a chemical, physical, enzymatic, or optical analysis. The analyte can be any specific substance or component that one is desirous of detecting and/or measuring in a chemical, physical, enzymatic, or optical analysis. Such analytes include, but are not limited to, amino acids, enzyme substrates or products indicating a disease state or condition, other markers of disease states or conditions, drugs of abuse, therapeutic and/or pharmacologic agents (e.g., theophylline, anti-HIV drugs, lithium, anti-epileptic drugs, cyclosporin, chemotherapeutics), electrolytes, physiological analytes of interest (e.g., urate/uric acid, carbonate, calcium, potassium, sodium, chloride, bicarbonate ($CO_2$), glucose, urea (blood urea nitrogen), lactate/lactic acid, hydroxybutyrate, cholesterol, triglycerides, creatine, creatinine, insulin, hematocrit, and hemoglobin), blood gases (carbon dioxide, oxygen, pH), lipids, heavy metals (e.g., lead, copper), and the like. In preferred embodiments, the analyte is a physiological analyte of interest, for example glucose, or a chemical that has a physiological action, for example a drug or pharmacological agent.

Thus, one embodiment of the invention provides a tri-layer collection assembly for use in a transdermal sampling device. The collection assembly is formed from a series of functional layers including: (1) a first surface layer that is comprised of a substantially planar material that has an opening which extends therethrough; (2) a second surface layer that is also comprised of a substantially planar material and has an opening therein; and (3) an intervening layer that is positioned between the first and second surface layers, wherein the intervening layer is comprised of an ionically conductive material. The first and second surface layers overlap the intervening layer at corresponding positions, and contact each other at their corresponding overlaps, such overlaps can be used to form a laminate structure. The openings in the first and second surface layers are axially aligned to provide a flow path through the laminate (i.e., a flow path that extends between the two surfaces and passes through the intervening layer). The overhangs provided by the mask and retaining layers are generally contacted with each other to sandwich the collection insert therebetween and form the assembly.

It is a related object of the invention to provide an autosensor assembly for use in a transdermal sampling device, wherein the assembly comprises the three functional layers of the above-described collection assembly or laminate, an electrode assembly, and, typically, a support tray.

It is a further object of the invention to provide a two layer collection assembly or laminate for use in a transdermal sampling device. The collection assembly is formed from two functional layers including: (1) a surface layer that is comprised of a substantially planar material that has an opening which extends therethrough; and (2) a second layer. The second layer is formed from the combination of a gasket and a collection insert. The gasket is comprised of a substantially planar material having a top face, a bottom face, and an opening extending between the top and bottom faces. The top face of the gasket is attached to the bottom face of the surface layer, and the opening in the gasket is axially aligned with the opening in the surface layer to provide a flow path through the laminate. The collection insert is arranged within and substantially fills the opening in the gasket such that the collection insert is aligned with the opening in the surface layer and rests against or is otherwise attached to a portion of the surface layer.

It is a related object of the invention to provide an autosensor assembly for use in a transdermal sampling device, wherein the assembly comprises the two layers of the above-described collection assembly or laminate, an electrode assembly with which the collection assembly is functionally aligned, and, typically, a support tray.

Thus, in one embodiment, the invention relates to a collection assembly for use in a iontophoretic sampling device useful to monitor a selected analyte or derivatives thereof present in a biological system. The collection assembly comprises:

a) a collection insert layer comprised of an ionically conductive material having first and second portions, each portion having first and second surfaces, b) a mask layer comprised of a material that is substantially impermeable to the selected analyte or derivatives thereof, wherein the mask layer (i) has inner and outer faces and said outer face provides contact with said biological system and the inner face is positioned in facing relation with the first surface of each collection insert, (ii) defines first and second openings that are aligned with the first and second portions of the collection insert layer, (iii) each opening exposes at least a portion of the first surface of the collection insert layer, and (iv) has a border which extends beyond the first surface of each portion of the collection insert layer to provide an overhang; and c) a retaining layer having (i) inner and outer faces wherein the inner face is positioned in facing relation with the second surface of each collection insert, (ii) defines first and second openings that are aligned with the first and second portions of the collection insert layer, (iii) each opening exposes at least a portion of the second surface of the collection insert layer, and (iv) has a border which extends beyond the first surface of each portion of the collection insert layer to provide an overhang.

In certain embodiments, the collection insert layer further comprises a gasket layer and the gasket layer is between the mask layer and the retaining layer.

In additional embodiments, the subject invention is directed to a laminate comprising a collection assembly, as described above, as well as a sealed package containing the laminate.

In still another embodiment, the invention is directed to an autosensor assembly for use in a iontophoretic sampling device useful to monitor an analyte present in a biological system. The autosensor assembly comprises:

(I) a collection assembly which comprises, a) a collection insert layer comprised of an ionically conductive material having first and second portions, each portion having first and second surfaces, b) a mask layer comprised of a substantially planar material that is substantially impermeable to the selected analyte or derivatives thereof, wherein the mask layer (i) has inner and outer faces and the outer face provides contact with the biological system and the inner face is positioned in facing relation with the first surface of each collection insert, (ii) defines first and second openings that are aligned with the first and second portions of the collection insert layer, (iii) each opening exposes at least a portion of the first surface of the collection insert layer, and (iv) has a border which extends beyond the first surface of each portion of the collection insert layer to provide an overhang;

(c) a retaining layer having (i) inner and outer faces wherein the inner face is positioned in facing relation with the second surface of each collection insert, (ii) defines first and second openings that are aligned with the first and second portions of the collection insert layer, (iii) each opening exposes at least a portion of the second surface of the collection insert layer, and (iv) has a border which extends beyond the first surface of each portion of the collection insert layer to provide an overhang; and (d) where the first and second openings in the mask layer are positioned in the collection assembly such that they are aligned with the first and second openings in the retaining layer and thereby define a plurality of flow paths through said collection assembly;

(II) an electrode assembly having an inner and outer face, the inner face comprising first and second bimodal electrodes, wherein the first and second bimodal electrodes are aligned with the first and second openings in the retaining layer of the collection assembly; and (III) a support tray that contacts the outer face of the electrode assembly.

In alternative embodiments, the autosensor assembly further comprises a first removable liner attached to the outer face of the retaining layer, and/or a second removable liner attached to the outer face of the mask layer. In addition, a plowfold liner can be used, for example, between the electrode surfaces and the collection inserts.

In further embodiments, the invention is directed to a sealed package containing the autosensor assembly described above. The sealed package may also contain a hydrating insert.

In yet another embodiment, the invention is directed to a collection assembly for use in a iontophoretic sampling device useful to monitor a selected analyte, or derivatives thereof, present in a biological system. The collection assembly comprises:

a) a mask layer comprised of a substantially planar material that is substantially impermeable to the selected analyte or derivatives thereof, where the mask layer has inner and outer faces and the outer face provides contact with the biological system;

b) a collection insert layer comprised of an ionically conductive material having first and second surfaces, and c) the mask and collection insert layers are configured such that (i) at least a portion of the collection insert is exposed to provide contact with the biological system, and (ii) flow of the analyte through the first surface of the collection insert layer from the biological system is prevented by the mask layer for any portion of the first surface of the collection insert layer that is in contact with the inner face of the mask layer.

In another embodiment, the invention is directed to an autosensor assembly comprising (a) the collection assembly above, (b) an electrode assembly having an inner face comprising an electrode and an outer face, where the inner face of the electrode assembly and the collection assembly are aligned to define a plurality of flow paths through the collection assembly, and (c) a support tray that contacts the outer face of the electrode assembly.

Additional objects, advantages and novel features of the invention will be set forth in part in the description which follows, and in part will become apparent to those skilled in the art upon examination of the following, or may be learned by practice of the invention.

BRIEF DESCRIPTION OF THE DRAWINGS

FIG. 8F shows the general shape and dimensions of the liner for contacting the mask and collection inserts (i.e., a "patient liner"). FIG. 8G shows the general shape and dimensions of the second liner (i.e., a "plow-fold" liner), for contacting the retaining layer and collection inserts. FIG. 8H shows a composite figure of autosensor components in their proper order of stacking/assembly.

FIG. 9E shows the general shape and dimensions of the second liner (i.e., a "plow-fold" liner), for contacting the gel retaining layer and the collection inserts, typically eliminating contact between the collection inserts and the iontophoretic/counter electrodes and reference electrode prior to removal. Further, FIG. 9F shows the general shape and dimensions of the liner for contacting the mask layer and collection inserts (i.e., a "patient liner"). FIG. 9G shows a composite figure of autosensor components in their proper order of stacking/assembly.

DETAILED DESCRIPTION OF THE INVENTION

Figure 1A:
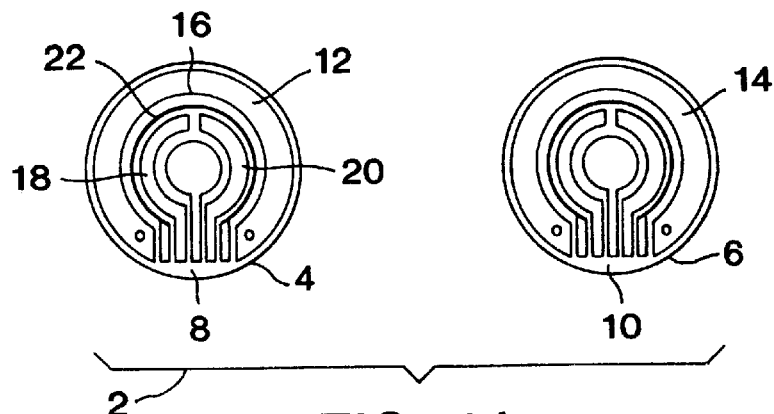
FIG. 1A depicts a top plan view of an iontophoretic collection reservoir and electrode assembly for use in a transdermal sampling device.

Before describing the present invention in detail, it is to be understood that this invention is not limited to particular compositions or biological systems as such may, of course, vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the content clearly dictates otherwise. Thus, for example, reference to "a collection insert" includes two or more such inserts, reference to "an analyte" includes a mixture of two or more such analytes, reference to "an electrochemically active species" includes two or more such species, and the like.

All publications, patents and patent applications cited herein, whether supra or infra, are hereby incorporated by reference in their entirety.

Unless defined otherwise, all technical and scientific terms used herein have the same meaning as commonly understood by one of ordinary skill in the art to which the invention pertains. Although any methods and materials similar or equivalent to those described herein can be used in the practice of the present invention, the preferred materials and methods are described herein.

In describing and claiming the present invention, the following terminology will be used in accordance with the definitions set out below.

1. DEFINITIONS

The terms "analyte" and "target analyte" are used herein to denote any physiological analyte of interest that is a specific substance or component that is being detected and/or measured in a chemical, physical, enzymatic, or optical analysis. A detectable signal (e.g., a chemical signal or electrochemical signal) can be obtained, either directly or indirectly, from such an analyte or derivatives thereof. Furthermore, the terms "analyte" and "substance" are used interchangeably herein, and are intended to have the same meaning, and thus encompass any substance of interest. In preferred embodiments, the analyte is a physiological analyte of interest, for example, glucose, or a chemical that has a physiological action, for example, a drug or pharmacological agent.

A "sampling device" or "sampling system" refers to any device for obtaining a sample from a biological system for the purpose of determining the concentration of an analyte of interest. As used herein, the term "sampling" means invasive, minimally invasive or non-invasive extraction of a substance from the biological system, generally across a membrane such as skin or mucosa. The membrane can be natural or artificial, and can be of plant or animal nature, such as natural or artificial skin, blood vessel tissue, intestinal tissue, and the like. Typically, the sampling means are in operative contact with a "reservoir," or "collection reservoir," wherein the sampling means is used for extracting the analyte from the biological system into the reservoir to obtain the analyte in the reservoir. A "biological system" includes both living and artificially maintained systems. Examples of minimally invasive and noninvasive sampling techniques include iontophoresis, sonophoresis, suction, electroporation, thermal poration, passive diffusion, microfine (miniature) lances or cannulas, subcutaneous implants or insertions, and laser devices. Sonophoresis uses ultrasound to increase the permeability of the skin (see, e.g., Menon et al. (1994) *Skin Pharmacology* 7:130–139). Suitable sonophoresis sampling systems are described in International Publication No. WO 91/12772, published Sep. 5, 1991. Passive diffusion sampling devices are described, for example, in International Publication Nos.: WO 97/38126 (published Oct. 16, 1997); WO 97/42888, WO 97/42886, WO 97/42885, and WO 97/42882 (all published Nov. 20, 1997); and WO 97/43962 (published Nov. 27, 1997). Laser devices use a small laser beam to burn a hole through the upper layer of the patient's skin (see, e.g., Jacques et al. (1978) *J. Invest. Dermatology* 88:88–93). Examples of invasive sampling techniques include traditional needle and syringe or vacuum sample tube devices.

A "housing" for the sampling system can further include suitable electronics (e.g., microprocessor, memory, display and other circuit components) and power sources for operating the sampling system in an automatic fashion.

A "monitoring system," as used herein, refers to a system useful for continually or continuously measuring a physiological analyte present in a biological system. Such a system typically includes, but is not limited to, sampling means, sensing means, and a microprocessor means in operative communication with the sampling means and the sensing means.

The term "artificial," as used herein, refers to an aggregation of cells of monolayer thickness or greater which are grown or cultured in vivo or in vitro, and which function as a tissue of an organism but are not actually derived, or excised, from a pre-existing source or host.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

As used herein, the term "continual measurement" intends a series of two or more measurements obtained from a particular biological system, which measurements are obtained using a single device maintained in operative contact with the biological system over the time period in which the series of measurements is obtained. The term thus includes continuous measurements.

The term "transdermal," as used herein, includes both transdermal and transmucosal techniques, i.e., extraction of a target analyte across skin or mucosal tissue. Aspects of the invention which are described herein in the context of "transdermal," unless otherwise specified, are meant to apply to both transdermal and transmucosal techniques.

The term "transdermal extraction," or "transdermally extracted" intends any noninvasive, or at least minimally invasive sampling method, which entails extracting and/or transporting an analyte from beneath a tissue surface across skin or mucosal tissue. The term thus includes extraction of an analyte using iontophoresis (reverse iontophoresis), electroosmosis, sonophoresis, microdialysis, suction, and passive diffusion. These methods can, of course, be coupled with application of skin penetration enhancers or skin permeability enhancing technique such as tape stripping or pricking with micro-needles. The term "transdermally extracted" also encompasses extraction techniques which employ thermal poration, electroporation, microfine lances, microfine canulas, subcutaneous implants or insertions, and the like.

The term "iontophoresis" intends a method for transporting substances across tissue by way of an application of electrical energy to the tissue. In conventional iontophoresis, a reservoir is provided at the tissue surface to serve as a container of material to be transported. Iontophoresis can be carried out using standard methods known to those of skill in the art, for example, by establishing an electrical potential using a direct current (DC) between fixed anode and cathode "iontophoretic electrodes," alternating a direct current between anode and cathode iontophoretic electrodes, or using a more complex waveform such as applying a current with alternating polarity (AP) between iontophoretic electrodes (so that each electrode is alternately an anode or a cathode).

The term "reverse iontophoresis" refers to the movement of a substance from a biological fluid across a membrane by way of an applied electric potential or current. In reverse iontophoresis, a reservoir is provided at the tissue surface to receive the extracted material.

"Electroosmosis" refers to the movement of a substance through a membrane by way of an electric field-induced convective flow. The terms iontophoresis, reverse iontophoresis, and electroosmosis, will be used interchangeably herein to refer to movement of any ionically charged or uncharged substance across a membrane (e.g., an epithelial membrane) upon application of an electric potential to the membrane through an ionically conductive medium.

The term "sensing device," "sensing means," or "biosensor device" encompasses any device that can be used to measure the concentration of an analyte, or derivative thereof, of interest. Preferred sensing devices for detecting blood analytes generally include electrochemical devices and chemical devices. Examples of electrochemical devices include the Clark electrode system (see, e.g., Updike, et al., (1967) *Nature* 214:986–988), and other amperometric, coulometric, or potentiometric electrochemical devices. Examples of chemical devices include conventional enzyme-based reactions as used in the Lifescan® glucose monitor (Johnson and Johnson, New Brunswick, N.J.) (see, e.g., U.S. Pat. No. 4,935,346 to Phillips, et al.).

A "biosensor" or "biosensor device" includes, but is not limited to, a "sensor element" which includes, but is not limited to, a "biosensor electrode" or "sensing electrode" or "working electrode" which refers to the electrode that is monitored to determine the amount of electrical signal at a point in time or over a given time period, which signal is then correlated with the concentration of a chemical compound. The sensing electrode comprises a reactive surface which converts the analyte, or a derivative thereof, to electrical signal. The reactive surface can be comprised of any electrically conductive material such as, but not limited to, platinum-group metals (including, platinum, palladium, rhodium, ruthenium, osmium, and iridium), nickel, copper, silver, and carbon, as well as, oxides, dioxides, combinations or alloys thereof. Some catalytic materials, membranes, and fabrication technologies suitable for the construction of amperometric biosensors were described by Newman, J. D., et al.(*Analytical Chemistry* 67(24), 4594–4599, 1995).

The "sensor element" can include components in addition to a biosensor electrode, for example, it can include a "reference electrode," and a "counter electrode." The term "reference electrode" is used herein to mean an electrode that provides a reference potential, e.g., a potential can be established between a reference electrode and a working electrode. The term "counter electrode" is used herein to mean an electrode in an electrochemical circuit which acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are most preferred.

In one embodiment, the "counter electrode" of the "sensor element" comprises a "bimodal electrode.-" The term "bimodal electrode" as used herein typically refers to an electrode which is capable of functioning non-simultaneously as, for example, both the counter electrode (of the "sensor element") and the iontophoretic electrode (of the "sampling means").

The terms "reactive surface," and "reactive face" are used interchangeably herein to mean the surface of the sensing electrode that: (1) is in contact with the surface of an electrolyte containing material (e.g. gel) which contains an analyte or through which an analyte, or a derivative thereof, flows from a source thereof; (2) is comprised of a catalytic material (e.g., carbon, platinum, palladium, rhodium, ruthenium, or nickel and/or oxides, dioxides and combinations or alloys thereof) or a material that provides sites for electrochemical reaction; (3) converts a chemical signal (e.g. hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal that is correlatable with the amount of analyte present in the electrolyte.

The term "collection reservoir" is used to describe any suitable containment means for containing a sample extracted from a biological system. For example, the collection reservoir can be a receptacle containing a material which is ionically conductive (e.g., water with ions therein), or alternatively, it can be a material, such as, a sponge-like material or hydrophilic polymer, used to keep the water in place. Such collection reservoirs can be in the form of a hydrogel (for example, in the form of a disk or pad). Hydrogels are typically referred to as "collection inserts." Other suitable collection reservoirs include, but are not limited to, tubes, vials, capillary collection devices, cannulas, and miniaturized etched, ablated or molded flow paths.

An "ionically conductive material" refers to any material that provides ionic conductivity, and through which electrochemically active species can diffuse. The ionically conductive material can be, for example, a solid, liquid, or semi-solid (e.g., in the form of a gel) material that contains an electrolyte, which can be composed primarily of water and ions (e.g., sodium chloride), and generally comprises 50% or more water by weight. The material can be in the form of a gel, a sponge or pad (e.g., soaked with an electrolytic solution), or any other material that can contain an electrolyte and allow passage therethrough of electrochemically active species, especially the analyte of interest.

The term "physiological effect" encompasses effects produced in the subject that achieve the intended purpose of a therapy. In preferred embodiments, a physiological effect means that the symptoms of the subject being treated are prevented or alleviated. For example, a physiological effect would be one that results in the prolongation of survival in a patient.

A "laminate", as used herein, refers to structures comprised of at least two bonded layers. The layers may be bonded by welding or through the use of adhesives. Examples of welding include, but are not limited to, the following: ultrasonic welding, heat bonding, and inductively coupled localized heating followed by localized flow. Examples of common adhesives include, but are not limited to, pressure sensitive adhesives, thermoset adhesives, cyanocrylate adhesives, epoxies, contact adhesives, and heat sensitive adhesives. An example of a laminate of the present invention is a mask layer, collection inserts, and a retaining layer (e.g., FIG. 3, 50) where at least the mask and retaining layer are bonded to each other.

A "collection assembly", as used herein, refers to structures comprised of several layers, where the assembly includes at least one collection insert, for example a hydrogel. An example of a collection assembly of the present invention is a mask layer, collection inserts, and a retaining layer (e.g., FIG. 3, 50) where the layers are held in appropriate, functional relationship to each other but are not necessarily a laminate, i.e., the layers may not be bonded together.

The layers may, for example, be held together by interlocking geometry or friction.

An "autosensor assembly", as used herein, refers to structures generally comprising a mask layer, collection inserts, a retaining layer, an electrode assembly, and a support tray. The autosensor assembly may also include liners (e.g., the autosensor assembly shown in FIG. 3) where the layers are held in appropriate, functional relationship to each other.

The mask and retaining layers are preferably composed of materials that are substantially impermeable to the analyte (chemical signal) to be detected (e.g., glucose); however, the material can be permeable to other substances. By "substantially impermeable" is meant that the material reduces or eliminates chemical signal transport (e.g., by diffusion). The material can allow for a low level of chemical signal transport, with the proviso that chemical signal that passes through the material does not cause significant edge effects at the sensing electrode.

"Substantially planar" as used herein, includes a slightly curved surface that conforms, for example, to the curvature of the forearm or upper arm of a subject. A "substantially planar" surface is, for example, a surface having a shape to which skin can conform, i.e., creating contact between the skin and the surface. A further example includes shapes that have large length and width relative to their depth (e.g., 10:1 or greater) and permit the skin to conform to their surface topography.

By the term "printed" as used herein is meant a substantially uniform deposition of an electrode formulation onto one surface of a substrate (i.e., the base support). It will be appreciated by those skilled in the art that a variety of techniques may be used to effect substantially uniform deposition of a material onto a substrate, e.g., Gravure-type printing, extrusion coating, screen coating, spraying, painting, or the like.

2. EXEMPLARY EMBODIMENTS OF SAMPLING SYSTEMS.

The present invention relates to laminates, collection assemblies, and other components useful in a sampling device for transdermally extracting and measuring the concentration of a target analyte present in a biological system. Such sampling devices are generally used for extracting small amounts of a target analyte from the biological system, and then sensing and/or quantifying the concentration of the target analyte. Measurement and/or sampling with the sampling device can be carried out in a continual or continuous manner. Continual or continuous measurements allow for closer monitoring of target analyte concentration fluctuations. In general, the sampling device comprises a biosensor with an electrochemical sensing element, and the sampling device is preferably used to perform continual transdermal or transmucosal sampling of blood glucose.

The analyte can be any specific substance or component that one is desirous of detecting and/or measuring in a chemical, physical, enzymatic, or optical analysis. Such analytes include, but are not limited to, amino acids, enzyme substrates or products indicating a disease state or condition, other markers of disease states or conditions, drugs of abuse, therapeutic and/or pharmacologic agents (e.g., theophylline, anti-HIV drugs, lithium, anti-epileptic drugs, cyclosporin, chemotherapeutics), electrolytes, physiological analytes of interest (e.g., urate/uric acid, carbonate, calcium, potassium, sodium, chloride, bicarbonate ($CO_2$), glucose, urea (blood urea nitrogen), lactate/lactic acid, hydroxybutyrate, cholesterol, triglycerides, creatine, creatinine, insulin, hematocrit, and hemoglobin), blood gases (carbon dioxide, oxygen, pH), lipids, heavy metals (e.g., lead, copper), and the like. In preferred embodiments, the analyte is a physiological analyte of interest, for example glucose, or a chemical that has a physiological action, for example a drug or pharmacological agent.

In order to facilitate detection of the analyte, an enzyme can be disposed in the collection reservoir, or, if several collection reservoirs are used, the enzyme can be disposed in several or all of the reservoirs. The selected enzyme is capable of catalyzing a reaction with the extracted analyte (in this case glucose) to the extent that a product of this reaction can be sensed, e.g., can be detected electrochemically from the generation of a current which current is detectable and proportional to the concentration or amount of the analyte which is reacted. A suitable enzyme is glucose oxidase which oxidizes glucose to gluconic acid and hydrogen peroxide. The subsequent detection of hydrogen peroxide on an appropriate biosensor electrode generates two electrons per hydrogen peroxide molecule which create a current which can be detected and related to the amount of glucose entering the device. Glucose oxidase (GOx) is readily available commercially and has well known catalytic characteristics. However, other enzymes can also be used, so long as they specifically catalyze a reaction with an analyte or substance of interest to generate a detectable product in proportion to the amount of analyte so reacted.

In like manner, a number of other analyte-specific enzyme systems can be used in the invention, which enzyme systems operate on much the same general techniques. For example, a biosensor electrode that detects hydrogen peroxide can be used to detect ethanol using an alcohol oxidase enzyme system, or similarly uric acid with urate oxidase system, urea with a urease system, cholesterol with a cholesterol oxidase system, and theophylline with a xanthine oxidase system.

In addition, the oxidase enzyme (used for hydrogen peroxide-based detection) can be replaced with another redox system, for example, the dehydrogenase-enzyme NAD-NADH, which offers a separate route to detecting additional analytes. Dehydrogenase-based sensors can use working electrodes made of gold or carbon (via mediated chemistry). Examples of analytes suitable for this type of monitoring include, but are not limited to, cholesterol, ethanol, hydroxybutyrate, phenylalanine, triglycerides, and urea. Further, the enzyme can be eliminated and detection can rely on direct electrochemical or potentiometric detection of an analyte. Such analytes include, without limitation, heavy metals (e.g., cobalt, iron, lead, nickel, zinc), oxygen, carbonate/carbon dioxide, chloride, fluoride, lithium, pH, potassium, sodium, and urea. Also, the sampling system described herein can be used for therapeutic drug monitoring, for example, monitoring anti-epileptic drugs (e.g., phenytion), chemotherapy (e.g., adriamycin), hyperactivity (e.g., ritalin), and anti-organ-rejection (e.g., cyclosporin).

More specifically, a non-invasive glucose monitoring (sampling) device is used to measure changes in glucose levels in an animal subject over a wide range of glucose concentrations. The sampling method is based on transdermal glucose extraction, and the sensing method is based on electrochemical detection technology. The device can be contacted with the biological system continuously, and automatically obtains glucose samples in order to measure glucose concentration at various selected intervals.

Sampling is carried out continually by non-invasively extracting glucose through the skin of the patient. More particularly, an iontophoretic current is applied to a surface of the skin of a subject. When the current is applied, ions or charged molecules pull along other uncharged molecules or particles such as glucose which are drawn into a collection insert placed on the surface of the skin. The collection insert may comprise any ionically conductive material and is preferably in the form of a hydrogel which is comprised of a hydrophilic material, water and an electrolyte.

The collection insert may further contain an enzyme which catalyzes a reaction of glucose to form an easily detectable species. The enzyme is preferably glucose oxidase (GOx) which catalyzes the reaction between glucose and oxygen and results in the production of hydrogen peroxide. The hydrogen peroxide reacts at a catalytic surface of a biosensor electrode, resulting in the generation of electrons which create a detectable biosensor current (raw signal). Based on the amount of biosensor current created over a given period of time, a measurement is taken, which measurement is related to the amount of glucose drawn into the collection insert over a given period of time.

When the reaction is complete, the process can be repeated and a subsequent measurement obtained. More specifically, the iontophoretic current is again applied, glucose is drawn through the skin surface into the collection insert, and the reaction is catalyzed in order to create a biosensor current. These sampling (extraction) and sensing operations can be integrated such that glucose is extracted into a hydrogel collection pad where it contacts the GOx enzyme. The GOx enzyme converts glucose and oxygen in the hydrogel to hydrogen peroxide which diffuses to the sensor and is catalyzed by the sensor to regenerate oxygen and form electrons. The electrons generate an electrical signal that can be measured, analyzed, and correlated to blood glucose.

In one embodiment of the present invention, the sampling system can have two collection reservoirs which contain, for example, an active collection reservoir, having the GOx enzyme, and a blank collection reservoir (without the GOx enzyme); or, in an alternative, two active reservoirs, i.e., two reservoirs containing the GOx enzyme. In the case of an active collection reservoir and a blank collection reservoir signal can be adjusted by subtraction of the blank reservoir signal from the signal obtained from the active reservoir. In the case of two active collection reservoirs the signals can be summed and averaged, or a total of the two signals can be used. This signal, for example the detected current, is then used alone or in combination with other factors (for example, glucose concentration at a calibration point, skin temperature, conductivity, voltage, time since calibration of the system, etc.) to provide a glucose concentration value.

In particular embodiments, the detected current can be correlated with the subject's blood glucose concentration (typically using statistical algorithms associated with a microprocessor) so that the system controller may display the subject's actual blood glucose concentration as measured by the sampling system. For example, the system can be calibrated to the subject's actual blood glucose concentration by sampling the subject's blood during a standard glucose tolerance test, and analyzing the blood glucose using both a standard blood glucose monitor and the sampling system of the present invention. In addition or alternately, the sampling system can be calibrated at a calibration time point where the signal obtained from the sampling system at that time point is correlated to blood glucose concentration at that time point as determined by direct blood testing (for example, glucose concentration can be determined using a HemoCue® clinical analyzer (HemoCue AB, Sweden)). In this manner, measurements obtained by the sampling system can be correlated to actual values using known statistical techniques. Such statistical techniques can be formulated as algorithm(s) and incorporated in a microprocessor associated with the sampling system.

A generalized method for continual monitoring of a physiological analyte is disclosed in International Publication No. WO 97/24059, published Jul. 10, 1997, which publication is incorporated herein by reference. As noted in that publication, the analyte is extracted into a reservoir containing a hydrogel which is preferably comprised of a hydrophilic material of the type described in International Publication No. WO 97/02811, published Jan. 30, 1997, which publication is incorporated herein by reference. Suitable hydrogel materials include, but are not limited to, polyethylene oxide, polyacrylic acid, polyvinylalcohol and related hydrophilic polymeric materials combined with water to form an aqueous gel.

In the above non-invasive glucose monitoring device, a biosensor electrode is positioned against a surface of the hydrogel opposite the surface of the hydrogel which contacts the skin. The sensor electrode acts as a detector which detects current generated by hydrogen peroxide in the redox reaction, or more specifically detects current which is generated by the electrons generated by the redox reaction catalyzed by the reactive surface of the electrode (International Publication No. WO 96/00110, published Jan. 4, 1996, and International Publication No. WO 97/10499, published Mar. 2, 1997, which publications are also incorporated herein by reference).

Figure 1B:
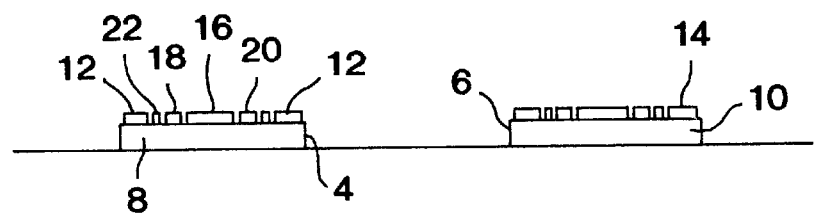
FIG. 1B depicts the side view of the iontophoretic collection reservoir and electrode assembly shown in FIG. 1A.

Referring now to FIGS. 1A and 1B, an exemplary iontophoretic collection reservoir and electrode assembly for use in a transdermal sensing device is generally indicated at 2. The assembly comprises two iontophoretic collection reservoirs, 4 and 6, each generally comprising a conductive medium 8, and 10 (preferably cylindrical hydrogel pads), respectively disposed therein. First (12) and second (14) ring-shaped iontophoretic electrodes are respectively contacted with conductive medium 8 and 10. The first iontophoretic electrode 12 surrounds three biosensor electrodes which are also contacted with the conductive medium 8, a working electrode 16, a reference electrode 18, and a counter electrode 20. A guard ring 22 separates the biosensor electrodes from the iontophoretic electrode 12 to minimize noise from the iontophoretic circuit. Conductive contacts provide communication between the electrodes and an associated power source and control means as described below. A similar biosensor electrode arrangement can be contacted with the conductive medium 10, or the medium may not have a sensor means contacted therewith (e.g., in order to provide a blank).

Figure 2:
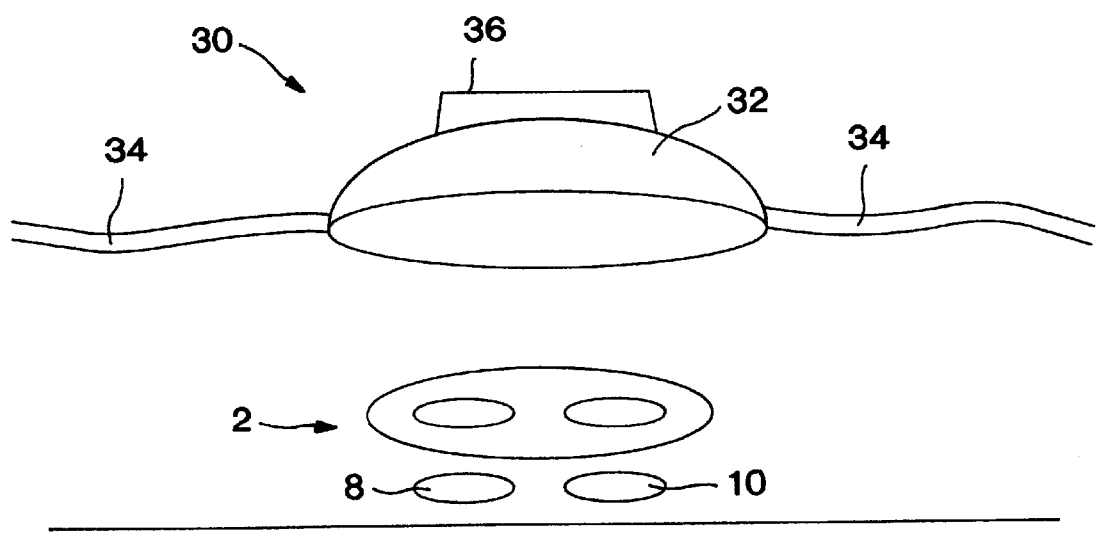
FIG. 2 is a pictorial representation of an iontophoretic sampling device which includes the iontophoretic collection reservoir and electrode assembly of FIGS. 1A and 1B.

Referring now to FIG. 2, the iontophoretic collection reservoir and electrode assembly 2 of FIGS. 1A and 1B is shown in exploded view in combination with a suitable iontophoretic sampling device housing 32. The housing can be a plastic case or other suitable structure which preferably is configured to be worn on a subject's arm in a manner similar to a wrist watch. As can be seen, conductive media 8 and 10 (hydrogel pads) are separable from the assembly 2; however, when the assembly 2 and the housing 32 are combined to provide an operational iontophoretic sampling device 30, the media are in contact with the electrodes to provide a electrical contact therewith.

A power source (e.g., one or more rechargeable or non-rechargeable batteries) can be disposed within the housing 32 or within the straps 34 which hold the device in contact with a skin or mucosal surface of a subject. In use, an electric potential (either direct current or a more complex waveform) is applied between the two iontophoretic electrodes 12 and 14 such that current flows from the first iontophoretic electrode 12, through the first conductive medium 8 into the skin or mucosal surface, and then back out through the second conductive medium 10 to the second iontophoretic electrode 14. The current flow is sufficient to extract substances including an analyte of interest through the skin into one or both of collection reservoirs 4 and 6. The electric potential may be applied using any suitable technique, for example, the applied current density may be in the range of about 0.01 to 0.5 mA/cm$^2$. In a preferred embodiment, the device is used for continual or continuous monitoring, and the polarity of iontophoretic electrodes 12 and 14 is alternated at a rate of about one switch every 10 seconds to about one switch every hour so that each electrode is alternately a cathode or an anode. After a suitable iontophoretic extraction period, one or both of the sensor electrode sets can be activated in order to detect extracted substances including the analyte of interest. Operation of the iontophoretic sampling device 30 is preferably controlled by a controller 36 (e.g., a microprocessor), which interfaces with the iontophoretic electrodes, the sensor electrodes, the power supply, as well as optional temperature and/or conductance sensing elements, a display, and other electronics. For example, the controller 36 can include a programmable controlled circuit source/sink drive for driving the iontophoretic electrodes. Power and reference voltage are provided to the sensor electrodes, and signal amplifiers can be used to process the signal from the working electrode or electrodes. In general, the controller discontinues the iontophoretic current drive during sensing periods.

In a further aspect of the above embodiments, the sensor element can also include a reference electrode, and a counter electrode. Further, a counter electrode of the sensor element and an iontophoretic electrode of the sampling system can be combined as a single bimodal electrode where the electrode is not used simultaneously for both functions, i.e., where the counter and iontophoretic functions are separately carried out at different times.

Figure 6:
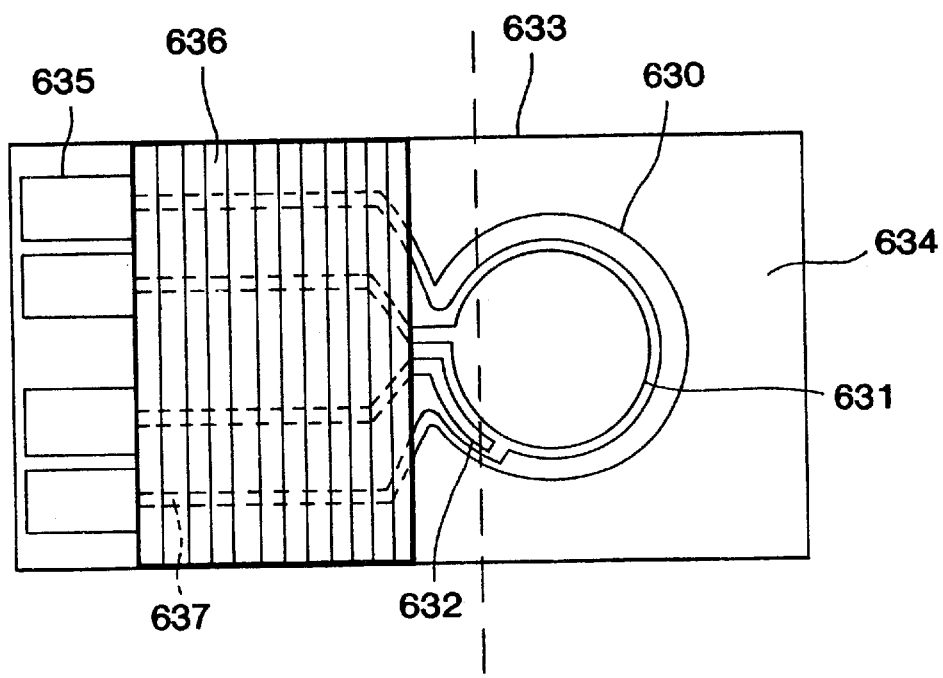
FIG. 6 is a representation of one embodiment of a bimodal electrode design. The figure presents an overhead and schematic view of the electrode assembly 633. In the figure, the bimodal electrode is shown at 630 and can be, for example, a Ag/AgCl iontophoretic/counter electrode. The sensing or working electrode (made from, for example, platinum) is shown at 631. The reference electrode is shown at 632 and can be, for example, a Ag/AgCl electrode. The components are mounted on a suitable nonconductive substrate 634, for example, plastic or ceramic. The conductive leads 637 leading to the connection pad 635 are covered by a second nonconductive piece 636 of similar or different material. In this example of such an electrode the working electrode area is approximately 1.35 cm$^2$. The dashed line in FIG. 6 represents the plane of the cross-sectional schematic view presented in FIG. 7.
Figure 7:
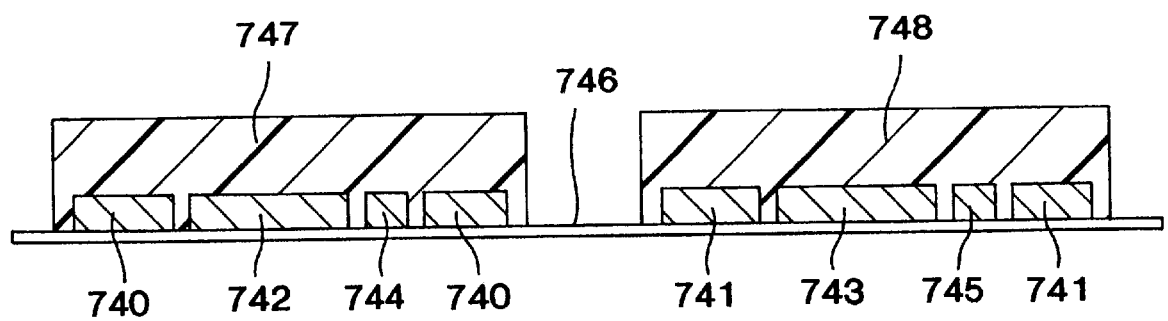
FIG. 7 is a representation of a cross-sectional schematic view of the bimodal electrodes as they may be used in conjunction with a reference electrode and a hydrogel pad. In the figure, the components are as follows: bimodal electrodes 740 and 741; sensing electrodes 742 and 743; reference electrodes 744 and 745; a substrate 746; and hydrogel pads 747 and 748.

In one aspect, the sampling device can operate in an alternating polarity mode, for example, using first and second bimodal electrodes (FIG. 7, 740 and 741) and two collection reservoirs (FIG. 7, 747 and 748). Each bi-modal electrode (FIG. 6, 630; FIG. 7, 740 and 741) serves two functions depending on the phase of the operation: (1) an electro-osmotic electrode (or iontophoretic electrode) used to electrically draw analyte from a source into a collection reservoir comprising water and an electrolyte, and to the area of the electrode subassembly; and (2) as a counter electrode to the first sensing electrode at which the chemical compound is catalytically converted at the face of the sensing electrode to produce an electrical signal.

The reference (FIG. 7, 744 and 745; FIG. 6, 632) and sensing electrodes (FIG. 7, 742 and 743; FIG. 6, 631), as well as, the bimodal electrode (FIG. 7, 740 and 741; FIG. 6, 630) are connected to a standard potentiostat circuit during sensing. In general, practical limitations of the system require that the bimodal electrode will not act as both a counter and iontophoretic electrode simultaneously.

The general operation of an iontophoretic sampling system is the cyclical repetition of two phases: (1) a reverse-iontophoretic phase, followed by a (2) sensing phase. During the reverse iontophoretic phase, the first bimodal electrode (FIG. 7, 740) acts as an iontophoretic cathode and the second bimodal electrode (FIG. 7, 741) acts as an iontophoretic anode to complete the circuit. Analyte is collected in the reservoirs, for example, a hydrogel (FIG. 7, 747 and 748). At the end of the reverse iontophoretic phase, the iontophoretic current is turned off. During the sensing phase, in the case of glucose, a potential is applied between the reference electrode (FIG. 7, 744) and the sensing electrode (FIG. 7, 742). The chemical signal reacts catalytically on the catalytic face of the first sensing electrode (FIG. 7, 742) producing an electrical current, while the first bi-modal electrode (FIG. 7, 740) acts as a counter electrode to complete the electrical circuit.

The electrode described is particularly adapted for use in conjunction with a hydrogel collection reservoir system for monitoring glucose levels in a subject through the reaction of collected glucose with the enzyme glucose oxidase present in the hydrogel matrix.

The bi-modal electrode is preferably comprised of Ag/AgCl; other suitable substances are can be determined in view of the teachings of the present disclosure and the prior art. The electrochemical reaction which occurs at the surface of this electrode serves as a facile source or sink for electrical current. This property is especially important for the iontophoresis function of the electrode. Lacking this reaction, the iontophoresis current could cause the hydrolysis of water to occur at the iontophoresis electrodes causing pH changes and possible gas bubble formation. The pH changes to acidic or basic pH could cause skin irritation or burns. The ability of an Ag/AgCl electrode to easily act as a source of sink current is also an advantage for its counter electrode function. For a three electrode electrochemical cell to function properly, the current generation capacity of the counter electrode should not limit the speed of the reaction at the sensing electrode. In the case of a large sensing electrode, the counter electrode should be able to source proportionately larger currents.

The design of the sampling system provides for a larger sensing electrode (see for example, FIG. 6) than previously designed. Consequently, the size of the bimodal electrode should be sufficient so that when acting as a counter electrode with respect to the sensing electrode the counter electrode does not become limiting the rate of catalytic reaction at the sensing electrode catalytic surface.

Two methods exist to ensure that the counter electrode does not limit the current at the sensing electrode: (1) the bi-modal electrode is made much larger than the sensing electrode, or (2) a facile counter reaction is provided.

During the reverse iontophoretic phase, the power source provides a current flow to the first bi-modal electrode to facilitate the extraction of the chemical signal into the reservoir. During the sensing phase, the power source is used to provide voltage to the first sensing electrode to drive the conversion of chemical signal retained in reservoir to electrical signal at the catalytic face of the sensing electrode. The power source also maintains a fixed potential at the electrode where, for example, hydrogen peroxide is converted to molecular oxygen, hydrogen ions, and electrons, which is compared with the potential of the reference electrode during the sensing phase. While one sensing electrode is operating in the sensing mode it is electrically connected to the adjacent bimodal electrode which acts as a counter electrode at which electrons generated at the sensing electrode are consumed.

The electrode sub-assembly can be operated by electrically connecting the bimodal electrodes such that each electrode is capable of functioning as both an iontophoretic electrode and counter electrode along with appropriate sensing electrode(s) and reference electrode(s), to create standard potentiostat circuitry.

A potentiostat is an electrical circuit used in electrochemical measurements in three electrode electrochemical cells. A potential is applied between the reference electrode and the sensing electrode. The current generated at the sensing electrode flows through circuitry to the counter electrode (i.e., no current flows through the reference electrode to alter its equilibrium potential). Two independent potentiostat circuits can be used to operate the two biosensors. For the purpose of the present sampling system, the electrical current measured at the sensing electrode subassembly is the current that is correlated with an amount of chemical signal.

With regard to continual operation for extended periods of time, Ag/AgCl electrodes are provided herein which are capable of repeatedly forming a reversible couple which operates without unwanted electrochemical side reactions (which could give rise to changes in pH, and liberation of hydrogen and oxygen due to water hydrolysis). The Ag/AgCl electrodes of the present sampling system are thus formulated to withstand repeated cycles of current passage in the range of about 0.01 to 1.0 mA per $cm^2$ of electrode area. With regard to high electrochemical purity, the Ag/AgCl components are dispersed within a suitable polymer binder. One such example of a suitable binder is styrene acrylonitrile (SAN) to provide an electrode composition which is not susceptible to attack (e.g., plasticization) by components in the collection reservoir, e.g., the hydrogel composition. The electrode compositions are also formulated using analytical- or electronic-grade reagents and solvents, and the polymer binder composition is selected to be free of electrochemically active contaminants which could diffuse to the biosensor to produce a background current.

Since the Ag/AgCl iontophoretic electrodes must be capable of continual cycling over extended periods of time, the absolute amounts of Ag and AgCl available in the electrodes, and the overall Ag/AgCl availability ratio, can be adjusted to provide for the passage of high amounts of charge. Although not limiting in the sampling system described herein, the Ag/AgCl ratio can approach unity. In order to operate within the preferred system which uses a biosensor having a geometric area of 0.1 to 3 $cm^2$, the iontophoretic electrodes are configured to provide an approximate electrode area of 0.3 to 1.0 $cm^2$, preferably about 0.85 $cm^2$. These electrodes provide for reproducible, repeated cycles of charge passage at current densities ranging from about 0.01 to 1.0 $mA/cm^2$ of electrode area. More particularly, electrodes constructed according to the above formulation parameters, and having an approximate electrode area of 0.85 $cm^2$, are capable of a reproducible total charge passage (in both anodic and cathodic directions) of 270 mC, at a current of about 0.3 mA (current density of 0.35 $mA/cm^2$) for 48 cycles in a 24 hour period.

Once formulated, the Ag/AgCl electrode composition is affixed to a suitable rigid or flexible nonconductive surface (for example, polyester, polycarbonate, vinyl, acrylic, PETG (polyethylene terephthalate copolymer), PEN, and polyimide) as described above with respect to the biosensor electrode composition. A silver (Ag) underlayer is first applied to the surface in order to provide uniform conduction. The Ag/AgCl electrode composition is then applied over the Ag underlayer in any suitable pattern or geometry using various thin film techniques, such as sputtering, evaporation, vapor phase deposition, or the like, or using various thick film techniques, such as film laminating, electroplating, or the like. Alternatively, the Ag/AgCl composition can be applied using screen printing, pad printing, inkjet methods, transfer roll printing, or similar techniques. Preferably, both the Ag underlayer and the Ag/AgCl electrode are applied using a low temperature screen print onto a polymeric substrate, for example, polyester. This low temperature screen print can be carried out at about 125 to 160° C., and the screening can be carried out using a suitable mesh, ranging from about 100–400 mesh.

In one embodiment, the electrode assemblies can include bimodal electrodes as shown in FIG. 6 and described above.

The components described herein are intended for use in a automatic sampling device which is configured to be worn like an ordinary wristwatch. As described in International Publication No. WO 96/00110, published Jan. 4, 1996, the wristwatch housing typically contains conductive leads which communicate with the iontophoretic electrodes and the biosensor electrodes to control cycling and provide power to the iontophoretic electrodes, and to detect electrochemical signals produced at the biosensor electrode surfaces. The wristwatch housing can further include suitable electronics (e.g., microprocessor, memory, display and other circuit components) and power sources for operating the automatic sampling system.

Further, the sampling system can be pre-programmed to begin execution of its signal measurements (or other functions) at a designated time. One application of this feature is to have the sampling system in contact with a subject and to program the sampling system to begin sequence execution during the night so that it is available for calibration immediately upon waking. One advantage of this feature is that it removes any need to wait for the sampling system to warm-up before calibrating it.

3. LAMINATES, COLLECTION ASSEMBLIES, AND AUTOSENSOR ASSEMBLIES

The present invention relates to laminates, collection assemblies, and autosensors for use in a sampling device. More particularly, the present laminates, collection assemblies, and autosensors are used in a transdermal sampling device that is placed in operative contact with a skin or mucosal surface of the biological system to obtain a chemical signal associated with an analyte of interest. The sampling device transdermally extracts the analyte from the biological system using, for example, an iontophoretic sampling technique. The transdermal sampling device can be maintained in operative contact with the skin or mucosal surface of the biological system to provide such continual or continuous analyte measurement.

In one aspect, the invention relates to a collection assembly for use in a iontophoretic sampling device useful to monitor a selected analyte, or derivatives thereof, present in a biological system. The collection assembly can include:
 a) a mask layer comprised of a substantially planar material that is substantially impermeable to the selected analyte or derivatives thereof, where the mask layer has inner and outer faces and the outer face provides contact with the biological system;
 b) a collection insert layer comprised of an ionically conductive material having first and second surfaces, and
 c) the mask and collection insert layers are configured such that (i) at least a portion of the collection insert is exposed to provide contact with the biological system, and (ii) flow of the analyte through the first surface of the collection insert layer from the biological system is prevented by the mask layer for any portion of the first surface of the collection insert layer that is in contact with the inner face of the mask layer. Such collection assemblies can be included in autosensor assemblies typically including (a) the collection assembly, (b) an electrode assembly having an inner face comprising an electrode and an outer face, where the inner face of the electrode assembly and the collection assembly are aligned to define a plurality of flow paths through said collection assembly, and (c) a support tray that contacts the outer face of the electrode assembly. One example of this type of collection assembly and autosensor assembly is described in Example 2.

In a further aspect, the invention includes a collection assembly having a mask layer, a collection insert layer comprised of an ionically conductive material, wherein the layers are axially aligned to provide a flow path through the collection assembly. Typically, the mask layer is comprised of a material that is substantially impermeable to the chemical signal associated with the analyte of interest. Exemplary embodiments of such collection assemblies are described in Examples 1 and 2. Example 1 describes use of a retaining layer as well.

In one embodiment, the mask layer and retaining layer each define at least one opening and at least a portion of a collection insert is exposed by each opening to provide a flow path through the collection assembly. Further, the collection insert may be contained by a corral or gasket that contains, seals, or retains the collection insert at a desired location. When a gasket is used the entire surface of the collection insert may be exposed, for example, by the mask layer. In this case the mask layer contacts the edges of the gasket.

In another embodiment, the mask layer and retaining layer each define two openings and at least a portion of a collection insert is exposed by each opening to provide two flow paths through the collection assembly. As stated above, the collection inserts may each be contained by a corral or gasket.

The mask layer may be coated with an adhesive on either of its faces or on both of its faces. Further, a liner may be adhered to one of the faces of the mask layer, typically the outer face. Similarly for the retaining layer. In one embodiment, (i) the outer face of the mask layer has an adhesive coating and a liner attached, (ii) the inner face of the mask layer contacts the collection inserts and adheres to the inner face of the retaining layer, and (iii) the outer face of the retaining layer is adhered to a second liner (e.g., a plow-fold liner).

The collection assemblies may be prepared as laminates. Further, other components, such as support trays and electrodes or electrode assemblies can be combined with the collection assemblies or laminates to form autosensor assemblies.

Further, the collection assemblies, laminates, and autosensors of the invention may be provided in sealed packages. Such sealed packets may further comprise a source of hydration (e.g., a hydrating insert) which ensures that the collection inserts will not dehydrate prior to use.

Figure 3:
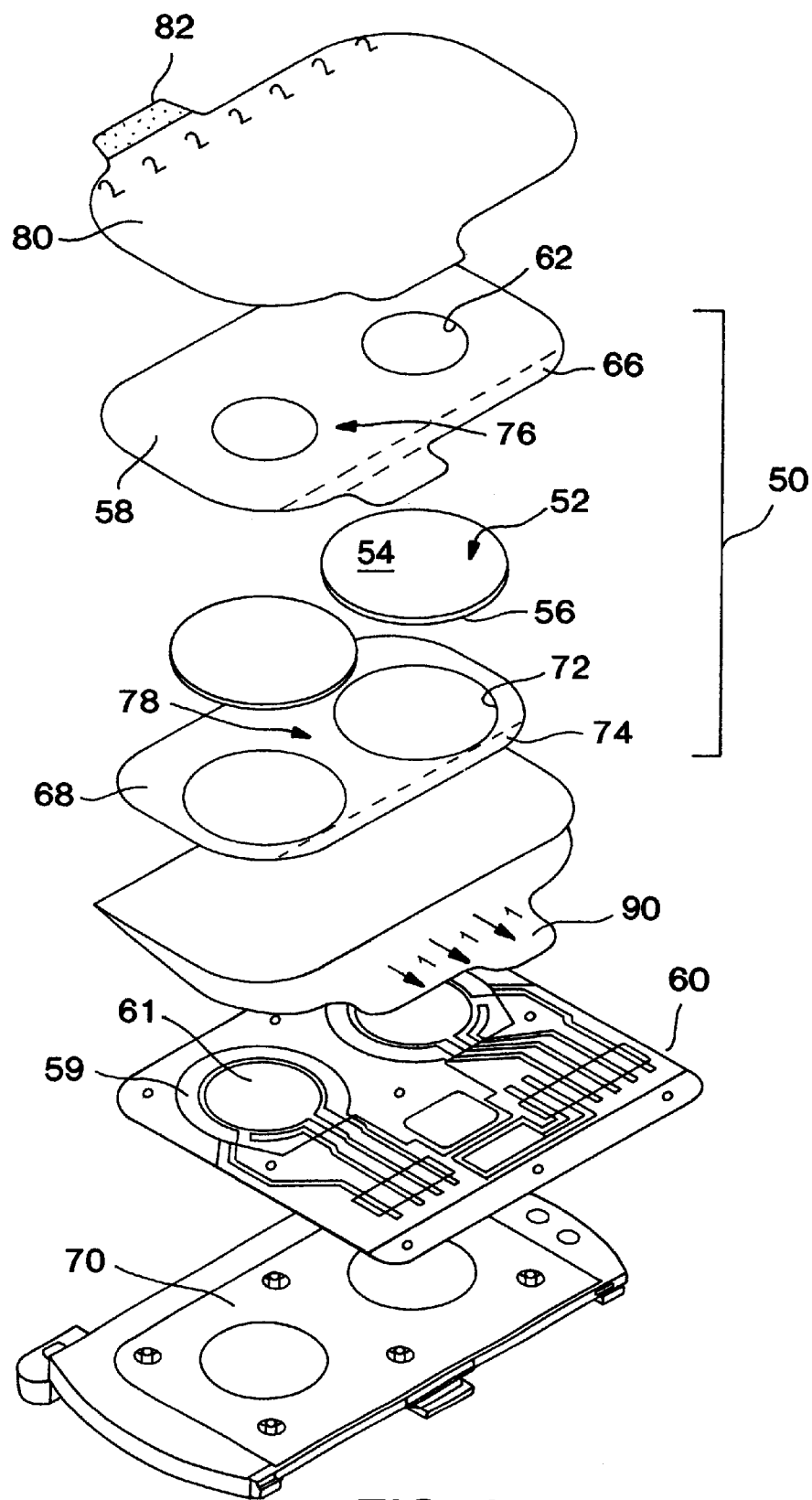
FIG. 3 depicts an exploded view of one embodiment of a collection assembly and autosensor constructed according to the present invention.

The collection assemblies, laminates, and autosensors of the present invention are particularly well suited for use as consumable components in the iontophoretic sampling device of FIG. 2. Referring now to FIG. 3, one embodiment of a collection assembly for use in such a sampling device is generally indicated at 50. The assembly is aligned with an electrode assembly 60 which includes both iontophoretic 59 and sensing electrodes 61 as described above. A tray 70 is adapted to hold the electrode and collection assemblies in operative alignment, and provides electrical connection between the electrode assembly and control components provided by an associated housing element (e.g., housing 32 of FIG. 2). If desired, the tray 70 can be comprised of a substantially rigid substrate and have features or structures which cooperate and/or help align the various assemblies in the sampling device. For example, the tray can have one or more wells or recesses, and/or one or more lips, rims, or other structures which depend from the substrate, each of which features or structures facilitate register between the electrode assembly, the collection assembly and the associated components of the sampling device. The tray can be composed of any suitable material, desirable characteristics of which can include the following: (i) high heat distortion temperature (to allow hot melt bonding of the electrode assembly to the tray, if necessary or desired); (ii) optimum rigidity, to allow for ease of handling and insertion into the housing of the monitoring device; (iii) low moisture uptake, to insure that proper hydration of the ionically conductive medium (e.g., hydrogel collection inserts) is maintained when the medium is stored in proximity to the tray; and, (iv) moldable by conventional processing techniques, for example, injection molding.

Materials for use in manufacturing the tray include, but are not limited to, the following: PETG (polyethylene terephthalate copolymer); ABS (acrylonitrile-butadiene-styrene co-polymer); SAN (styrene-acrylonitrile copolymer); SMA (styrene-maleic anhydride copolymer); HIPS (high impact polystyrene); polyethylene terephthalate (PET); polystyrene (PS); polypropylene (PP); and blends thereof. In a preferred embodiment the tray is formed from high impact polystyrene.

The electrode assembly is typically fixed to the tray to, for example, facilitate register between the electrode assembly and the associated components of the housing of the sampling device. The electrode assembly may be manufactured as part of the tray, or, the electrode assembly may be attached to the tray by, for example, (i) using connecting means which allow the electrode assembly to engage the tray (e.g., holes in the electrode assembly with corresponding pegs on the tray); or (ii) use of an adhesive. Exemplary adhesives include, but are not limited to, the following: acrylate, cyanoacrylate, styrene-butadiene, co-polymer based adhesives, and silicone. In a preferred embodiment the tray is attached to the electrode assembly as in (i) above with the pegs deformed, thus locking the components together.

The collection assembly 50 includes one or more collection inserts 52 that are comprised of an tonically conductive material. Each collection insert has first and second opposing surfaces, 54 and 56, respectively. The collection insert is preferably comprised of a substantially planar hydrogel disk. The first opposing surface 54 of the insert is intended for contact with a target surface (skin or mucosa), and the second opposing surface 56 is intended for contact with the electrode assembly 60, thereby establishing a flow path between the target surface and the iontophoretic and sensing electrodes. A mask layer 58 is positioned over the first surface 54 of the collection insert. The mask layer is used to inhibit contact between the sensing electrode(s) of the electrode assembly and chemical signal that may be transported in a radial direction from the target surface. The mask layer 58 comprises at least one opening 62 which is sized to allow a detectable amount of chemical signal to reach the sensing electrode, while reducing or preventing entry of chemical signal into the flow path thorough the insert that has a potential to be transported (e.g., by diffusion) in a radial direction toward an edge of the sensing electrode. As explained in commonly owned U.S. Pat. No. 5,735,273, incorporated by reference herein, this type of mask layer serves to substantially eliminate "edge effect" flow, i.e., the mask prevents chemical signal from contacting the electrode unless the signal flows substantially perpendicular to the surface of the sensing electrode. Accordingly, the opening 62 in the mask layer is sized to expose at least a portion of the first surface 54 of the collection insert. In the particular embodiment depicted in FIG. 3, a border region 66 of the mask layer generally extends beyond the first surface of the collection insert to provide an overhang.

A retaining layer 68 is positioned in facing relation with the second surface 56 of the collection insert 52. The retaining layer has at least one opening 72 which exposes at least a portion of the second surface 56 of the collection insert. Again, in the particular embodiment of FIG. 3, a border region 74 of the retaining layer 68 extends beyond the second surface 56 in order to provide an overhang. The overhangs provided by the mask and retaining layers serve as a point of attachment between the two layers. When these layers are attached to each other at their overhanging portions, a laminate is formed wherein the collection insert is sandwiched between the two layers to provide a three-layer structure. Although the overhangs provided by border regions 66 and 74 are depicted in FIG. 3 as extending along an edge of the mask and retaining layers, the overhangs can, of course, be formed from one or more corresponding tab overhangs (positioned anywhere on the subject layers), one or more corresponding edges (opposite and/or adjacent edges), or can be formed from a continuous overhang which encompasses the collection insert (e.g., an overhang which circumscribes an oval-or circular-shaped insert, or an overhang which surrounds all sides of a square-, rectangular-, rhomboid-, or triangular-shaped insert).

The one or more openings 62 in the mask layer, and the one or more openings 72 in the retaining layer can have any suitable geometry which is generally dictated by the shape of the collection insert 52 and/or the shape of the iontophoretic and sensing electrodes 59 and 61 used in the electrode assembly 60. In the embodiment depicted in FIG. 31 wherein the electrodes are arranged in a circular configuration and the collection insert is a circular disk, openings 62 and 72 preferably have a round, oval, ellipsoid, or "D"-shape which serves to collimate the flow (i.e., reduce or eliminate the edge effect flow) of chemical signal as it passes through the collection assembly toward the electrode assembly 60.

The openings 62 and 72 in the mask and retaining layers can be sized the same or differently, wherein the particular sizes of the openings are generally set by the overall surface area of the sensing electrode 61 that the collection assembly must operate with in the sensing device. Although the collection assemblies of the present invention can be provided in any size suitable for a targeted skin or mucosal surface, an assembly that is used with a sampling device that contacts a subject's wrist will generally have a surface area on each face in the range of about 0.5 $cm^2$ to 15 $cm^2$. The openings 62 and 72 generally expose about 50% of the area of the sensing electrode, within a manufacturing tolerance of about ±20%. In general, the openings constitute an area that is in the range of 1% to 90% of the surface area encompassed by the mask or retaining layer plus the opening(s). The openings are, however, sized smaller than the overall surface of the collection insert in at least one dimension.

The size or geometric surface area of the sensing electrode 61, the thickness of the collection insert 52, the sizes of the openings 62 and 72 in the mask and retaining layers, and the size of the overhangs provided by border regions 66 and 74 of the mask and retaining layers are all interrelated to each other. For example, when the thickness of the collection insert is increased, the size of the opening is decreased to obtain the same degree of reduction of edge effect flow (radial transport) of the transported chemical signal. Any decrease in the size of the openings in the mask and retaining layers increases the ability to block such unwanted flow. However, it is also desirable to maximize the size of the openings in order to maximize the amount of chemical signal which contacts the reactive surface of the sensing electrode 61.

The physical characteristics of the mask and retaining layers are selected so as to optimize the operational performance of the collection assembly. More particularly, since the assembly is intended to be contacted with a target surface for an extended period of time, the layers preferably have sufficient mechanical integrity so as to provide for such extended use. Furthermore, the layers should have sufficient flex and stretchability so as to resist tearing or rupture due to ordinary motion in the target surface, for example, movement of a subjects arm when the sampling device is contacted with a forearm or wrist. The layers can also have, for example, rounded corners which tolerate a greater degree of twist and flex in a target area (without breaking contact) than layers which have sharp, angular corners. The layers also provide for some degree of sealing between the target surface and the collection assembly 50, and between the collection assembly and the electrode assembly 60, and can provide for electrical, chemical, and/or electrochemical isolation between multiple collection inserts in the collection assembly and their corresponding electrodes in the electrode assembly. Other physical characteristics include the degree of occlusivity provided by the mask layer, adhesion to the target surface and/or electrode assembly, and mechanical containment of the associated collection insert(s). In one embodiment, the collection assembly includes two collection inserts (as depicted in FIG. 3), and the mask and retaining layers have corresponding central regions, 76 and 78, respectively, which are disposed between corresponding openings in the layers and provide for a further point of attachment between the two layers. As will be appreciated by the skilled artisan upon reading the present specification, this further point of attachment provides for chemical and electrical isolation between the two collection inserts.

The mask and retaining layers are preferably composed of materials that are substantially impermeable to the analyte (chemical signal) to be detected (e.g., glucose); however, the material can be permeable to other substances. By "substantially impermeable" is meant that the material reduces or eliminates chemical signal transport (e.g., by diffusion). The material can allow for a low level of chemical signal transport, with the proviso that chemical signal that passes through the material does not cause significant edge effects at the sensing electrode used in conjunction with the mask and retaining layers. Examples of materials that can be used to form the layers include, without limitation, the following: polymeric materials—such as, polyethylene (PE) {including, high density polyethylene (HDPE), low density polyethylene (LDPE), and very low density polyethylene (VLDPE)}, polyethylene copolymers, thermoplastic elastomers, silicon elastomers, polyurethane (PU), polypropylene (PP), (PET), nylon, flexible polyvinylchloride (PVC), and the like; natural rubber or synthetic rubber, such as latex; and combinations of the foregoing materials. Of these materials, exemplary flexible materials include, but are not limited to, the following: HDPE, LDPE, nylon, PET, PP, and flexible PVC. Stretchable materials include, but are not limited to, VLDPE, PU, silicone elastomers, and rubbers (e.g., natural rubbers, synthetic rubbers, and latex). In addition, adhesive materials, for example, acrylate, styrene butadiene rubber (SBR) based adhesives, styrene-ethylene-butylene rubber (SER) based adhesives, and similar pressure sensitive adhesives, can be used to form layers as well.

Each layer can be composed of a single material, or can be composed of two or more materials (e.g., multiple layers of the same or different materials) to form a chemical signal-impermeable composition.

Use of a mask to reduce or eliminate chemical signal which can radially transport toward a working electrode was described in co-owned U.S. Pat. Nos. 5,735,273 and 5,827,183, both herein incorporated by reference in their entireties.

Methods for making the mask and retaining layers include, without limitation, extrusion processes, flow and form molding techniques, die cutting, and stamping techniques, which are all practiced according to methods well known in the art. Most preferably, the layers are manufactured in a manner that is the most economical without compromising performance (e.g., impermeability to a chemical signal, the ability to manipulate the layers by hand without breaking or otherwise compromising operability, and the like). The layers may further have an adhesive coating (e.g., a pressure sensitive adhesive) on one or both surfaces. Exemplary adhesives include, but are not limited to, the following: starch, acrylate, styrene butadiene rubber-based, silicone, and the like. Adhesives that may come in contact with skin have a toxological profile compatible with skin-contact. In an exemplary embodiment, SBR-adhesive RP100 (John Deal Corporation, Mount Juliet, Tenn.) can be used on both sides of a 0.001 inch thick PET film (Melinex #329, DuPont) retaining layer to adhere to the mask and the other side to the sensor. Another exemplary embodiment uses acrylate #87–2196 (National Starch and Chemical Corporation, Bridgewater, N.J.) on the skin side of a 0.002 inch thick polyurethane (e.g., Dow Pellethane; Dow Chemical Corp., Midland, Mich.) mask to adhere the mask to the skin. Further, the mask and retaining layers may be coated with a material which absorbs one or more compounds or ions that may be extracted into the collection insert during sampling.

Since the collection assemblies of the present invention are intended for use as consumable (replaceable) components for a sampling device, the various constituents of the assemblies are preferably manufactured and then pre-assembled in an easy-to-use laminate structure that can be inserted and then removed from the sampling device housing by the consumer. In this regard, after the mask layer 58, retaining layer 68, and collection insert(s) 56 are produced, they are aligned as shown in FIG. 3, and the overhangs provided by borders 66 and 74 are attached to each other to provide a three-layer laminate which sandwiches the collection insert in between the mask and retaining layers as described above. The laminate, or a plurality of such laminates can be provided in a sealed package in order to maintain the cleanliness of the collection assembly (e.g., avoid chemical contamination from manufacturer and/or consumer handling) prior to use, and further to avoid dehydration of the collection inserts prior to use.

If desired, the package can include a source of hydration (e.g., a hydrating insert formed from a water-soaked pad, non-woven material, or gel which ensures that the collection inserts will not dehydrate prior to use. The hydrating insert may include other components as well, such as, buffers and antimicrobial compounds. The source of hydration is disposed of after the laminate has been removed from the package, and thus does not typically form a component of the sampling device.

The pre-assembled collection assembly laminates can include one or more optional liners which facilitate handling of the assembly. For example, a removable liner 80 can be applied over the mask layer 58, particularly when the mask layer is coated with an adhesive. An additional removable liner 90 can be applied over the retaining layer 68. The removable liners 80 and 90 are intended to remain in place until just prior to use of the assembly, and are thus manufactured from any suitable material which will not be too difficult to remove, but which will remain in place during packaging, shipment and storage to provide added protection to the assembly. If the mask and/or retaining layers are coated with (or actually formed from) an adhesive, the removable liners can preferably be comprised of a polypropylene or treated polyester material which does not adhere well to commonly used contact adhesives. Other suitable materials include, without limitation, water and/or solvent impermeable polymers (including, but not limited to PET, PP, PE, and the like) and treated metal foils.

The removable liners 80 and 90 are generally shaped to cover the outer surfaces of the mask and retaining layers. The liners can further include grasping means, such as the tab 82 depicted in FIG. 3, and intuitive indicia (such as numbering) which indicates the order in which the liners are intended to be removed during assembly of the sampling device. If desired, the liners can be shaped in a folded "V" (i.e., a "plow-fold" liner, see, e.g., liner 90 of FIG. 3) or "Z" shape which provides a grasping means for the user, as well as providing for a controlled release motion in the liner. Alternatively, the liners can have an internal cut (e.g., a spiral cut extending from one edge of the liner and ending in the surface of the liner) or a scoring pattern which facilitates removal of the liner. Particularly, the liner material, shape, and related cuts or patterns or weakness are selected to ensure that removal of the liners does not delaminate the collection assembly, or otherwise disrupt the alignment between the various components of the collection assembly (i.e., the alignment between the mask layer, retaining layer, and the collection insert).

Production of one embodiment of the above-described collection assembly and autosensor assembly is presented in Example 1.

Figure 4:
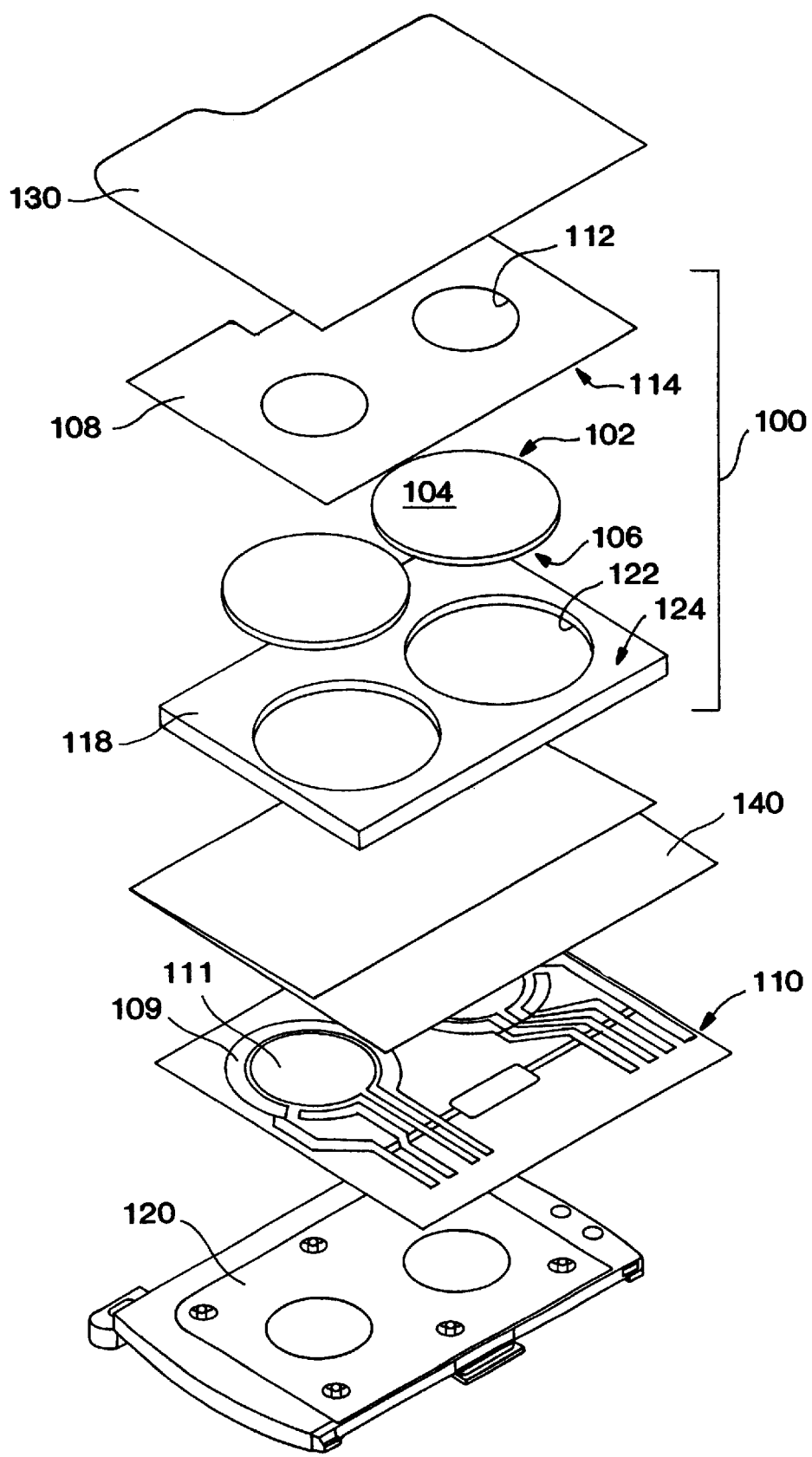
FIG. 4 depicts an exploded view of another embodiment of a collection assembly and autosensor constructed according to the present invention.

Referring now to FIG. 4, a related embodiment of a collection assembly produced according to the present invention is generally indicated at 100. The assembly 100 is aligned with an electrode assembly 110 which includes iontophoretic 109 and sensing electrodes 111 as described above, and is adapted to be held by a tray 120 as also described above. The collection assembly 100 includes one or more collection inserts 102 that are comprised of an ionically conductive material, and each collection insert has first and second opposing surfaces, 104 and 106, respectively.

The first opposing surface 104 of the collection insert 102 is intended for contact with a target surface (skin or mucosa), and the second opposing surface 106 is intended for contact with the electrode assembly 110, thereby establishing a flow path between the target surface and the iontophoretic and sensing electrodes. As above, a mask layer 108 is positioned over the first surface 104 of the collection insert, and includes one or more openings 112 which provide for a collimated flow path between the target surface and the electrode assembly as also described above. The opening 112 in the mask layer 108 is sized smaller in at least one dimension relative to the surface area of the collection insert 102.

A top surface 124 of a second layer 118 is positioned in facing relation with the bottom surface 114 of mask layer 108. The second layer comprises a gasket which has at least one opening 122. A two-layer laminate is formed when the mask and second layers are attached at their respective facing surfaces. The second layer also includes the collection insert 102 which is disposed within, and substantially fills the opening 122.

The physical and material properties of the mask layer are substantially identical to those of the mask layer described hereinabove, and the size and shape of the one or more openings are also determined using the above selection criteria. Furthermore, techniques for manufacture and manipulation of the mask layer 108 are substantially identical to those techniques described above. However, unlike the above-described retaining layer, the gasket in the second layer 118 of the present embodiment is intended to serve as a corral for the collection insert. More particularly, the gasket maintains the collection insert in a particular orientation such that, when the collection assembly is combined (contacted) with the electrode assembly, the collection insert is properly aligned with the iontophoretic and sensing electrodes. The gasket material further provides for electrical and/or chemical isolation between multiple collection inserts, and provides structure to the collection assembly.

The second layer gasket can be formed from any suitable material such as those materials used in the mask and retaining layers of the present invention. The gasket material could be a foam material that is sized to fit within the dimensions of the tray 120. Exemplary gasket materials include, without limitation, PE, PP, PET, nylon, and foamed PE. The gasket material can further have an adhesive coating or layer which contacts the electrode assembly and provides for the facile alignment between the electrode and collection assemblies.

Optional release liners 130 and/or 140 (a plow-fold liner) can also be respectively applied against the mask layer 108 and second layer 118 to facilitate handling of the collection assemblies as described above. Furthermore, pre-assembled collection assembly laminates are preferably packaged, either individually or in groups, as also previously described.

Figure 5:
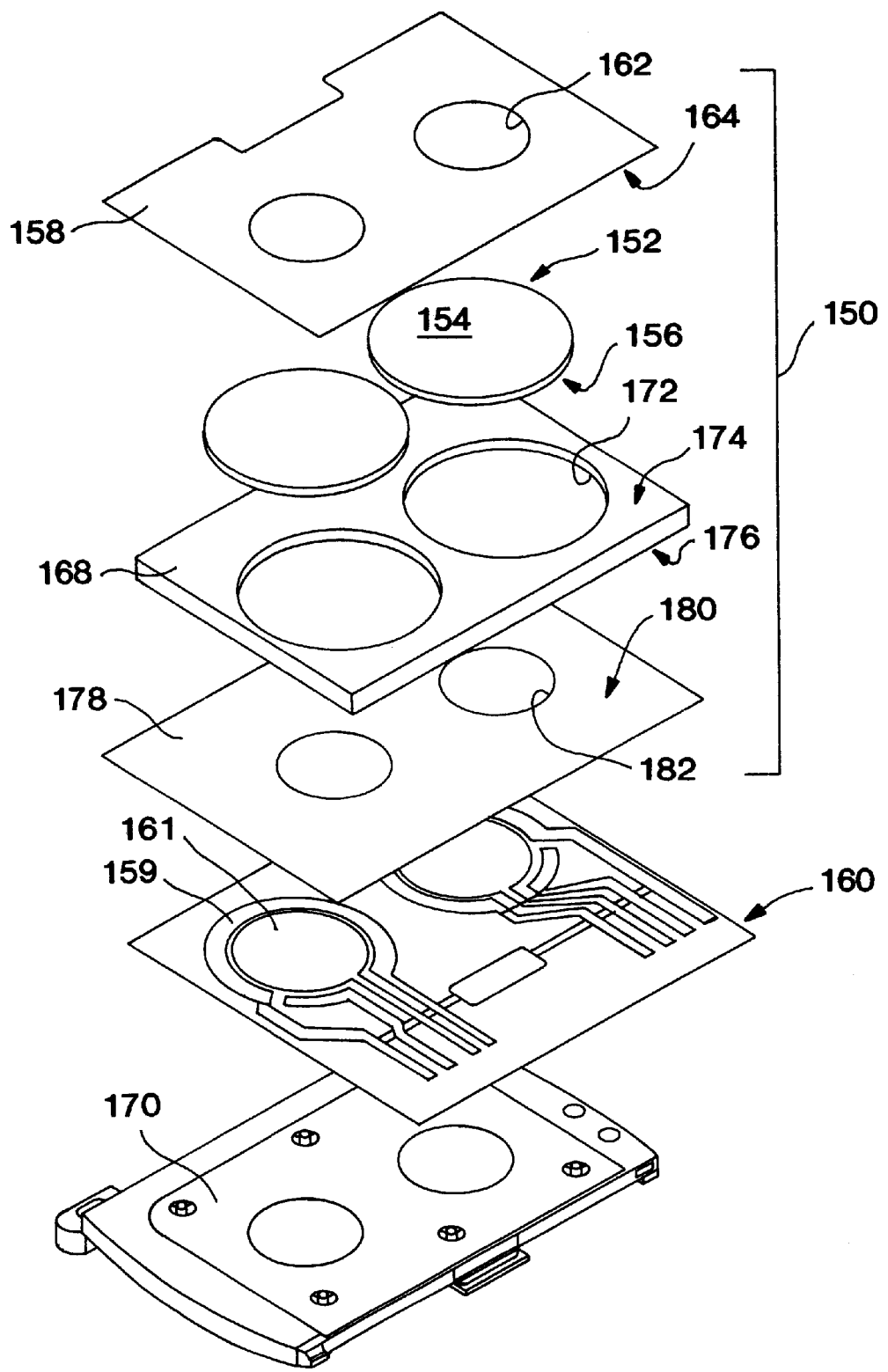
FIG. 5 depicts an exploded view of a still further embodiment of a collection assembly and autosensor constructed according to the present invention.

Referring now to FIG. 5, a still further related embodiment of a sampling system collection assembly is generally indicated at 150. The collection assembly 150 is aligned with an electrode assembly 160 which includes iontophoretic 159 and sensing electrodes 161 as described above, and is adapted to be held by a tray 170. The collection assembly 150 includes one or more collection inserts 152 that are comprised of an ionically conductive material, and each collection insert has first and second opposing surfaces, 154 and 156, respectively.

The first opposing surface 154 of the collection insert 152 is intended for contact with a target surface (skin or mucosa), and the second opposing surface 156 is intended for contact with the electrode assembly 120, thereby establishing a flow path between the target surface and the iontophoretic and sensing electrodes. As above, a mask layer 158 is positioned over the first surface 154 of the collection insert, and includes one or more openings 162 which provide for a collimated flow path between the target surface and the electrode assembly as also described above. The opening 162 in the mask layer 158 is sized smaller in at least one dimension relative to the surface area of the collection insert 152.

A top surface 174 of a second layer 168 is positioned in facing relation with the bottom surface 164 of the mask layer 158. The second layer comprises a gasket which has at least one opening 172. The second layer also includes the collection insert 152 which is disposed within, and substantially fills the opening 172.

The collection assembly 150 further includes a retaining layer 178, having a top surface 180 that is positioned in facing relation with the bottom surface 176 of the second layer 168. The retaining layer has at least one opening 182 which exposes at least a portion of the second surface 156 of the collection insert 152. When the corresponding surfaces of the mask layer and second layer are attached to each other, and the corresponding surfaces of the second layer and the retaining layer are attached to each other, a laminate is formed wherein both the second layer and the collection insert are sandwiched between the mask and retaining layers to provide a three-layer structure.

The physical and material properties of the mask and retaining layers are substantially identical to those of the mask and retaining layers described hereinabove, and the size and shape of the one or more openings are also determined using the above selection criteria. Furthermore, techniques for manufacture and manipulation of the mask and retaining layers 158 and 178 are substantially identical to those techniques described above. Furthermore, the physical and material properties of the second layer gasket are substantially identical to those described above.

Optional release liners can also be applied against the mask layer 158 and retaining layer 178 to facilitate handling of the collection assemblies as described above. Furthermore, pre-assembled collection assembly laminates are preferably packaged, either individually or in groups, as also previously described.

Experimental

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

In the following examples, efforts have been made to ensure accuracy with respect to numbers used (e.g., amounts, temperature, etc.) but some experimental error and deviation should be accounted for. Unless indicated otherwise, temperature is in degrees C and pressure is at or near atmospheric.

All patents, patent applications, and publications mentioned herein, both supra and infra, are hereby incorporated by reference.

Example 1

An Exemplary Autosensor Assembly

Figure 8A:
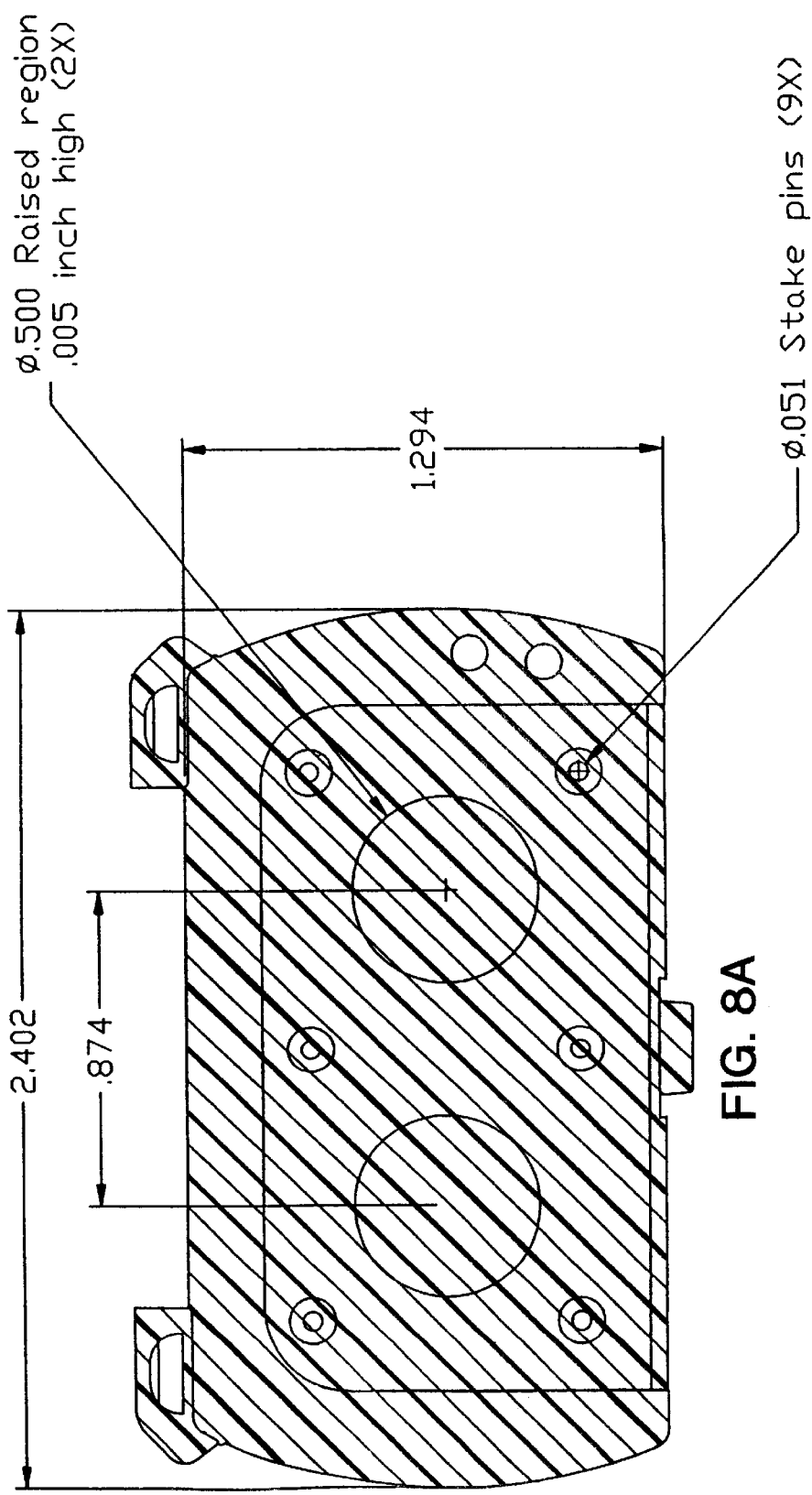
FIGS. 8A through 8H show general schematic diagrams for the components of one embodiment of an autosensor of the present invention. The general shape and dimensions of the tray are indicated in FIG. 8A. General shape and dimensions of the electrode assembly are indicated in FIG. 8B. A tri-layer laminate including a mask layer, having the general shape and dimensions shown in FIG. 8C, collection inserts, having the general shape and dimensions shown in FIG. 8D, and a retaining layer, having the general shape and dimensions shown in FIG. 8E. Further.

A tray was produced using a high impact polystyrene (e.g., Chevron Valtra HG200N02; Chevron Chemical Corp., Houston, Tex.) in a plastic injection molding process. General shape and dimensions of the tray are indicated in FIG. 8A (the tray was 0.110 inches thick, with raised areas indicated in the figure). Dimensions in FIGS. 8A to 8H are all given in inches.

Figure 8B:
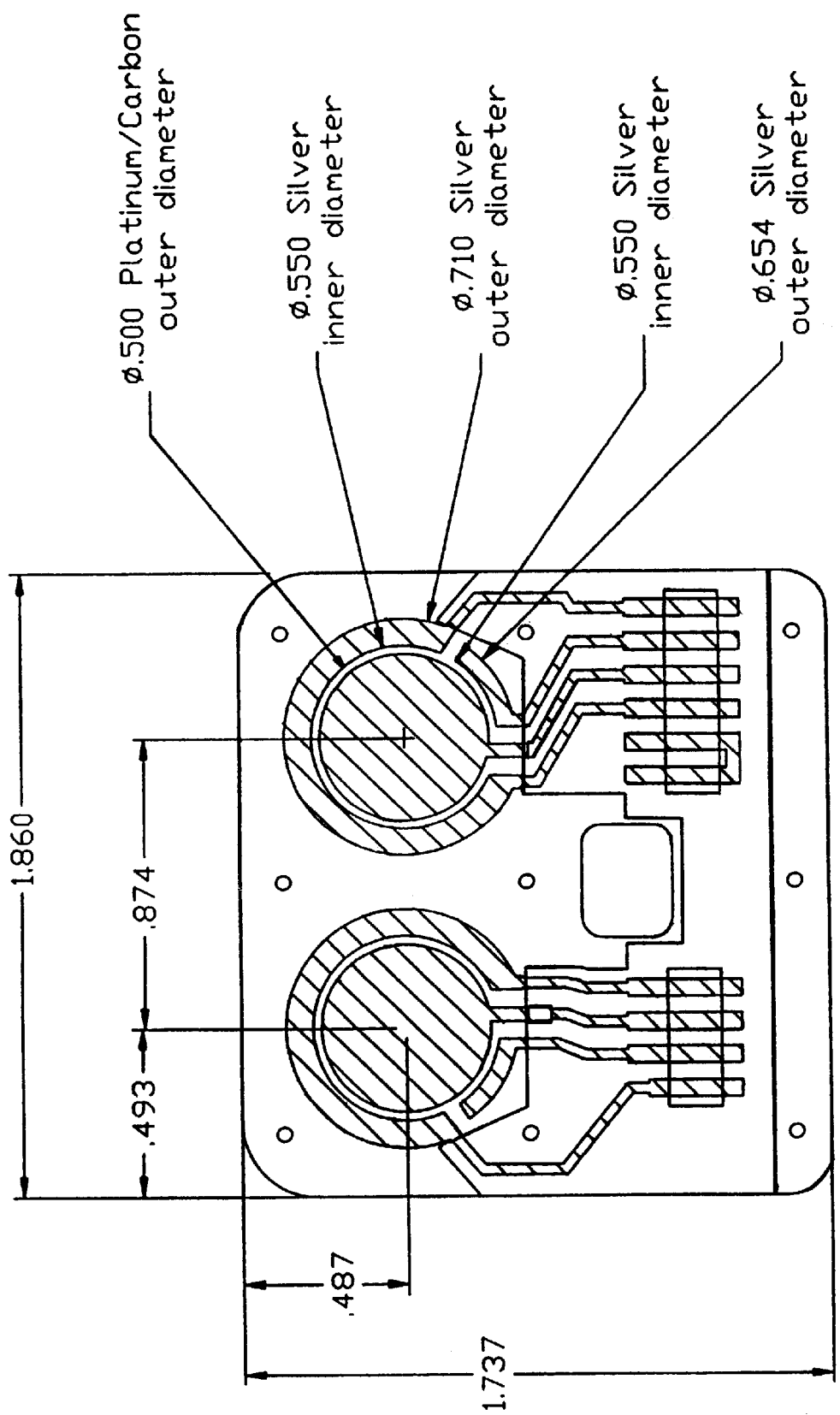

An electrode assembly was produced using thick film ink formulations in a screen printing process. Each ink formulation comprised: a) an electrically conductive particulate, b) an electrochemically active particulate, c) a polymeric binder, and d) a volatile organic solvent to create a liquid slurry. During screen printing, the inks were patterned onto the polyethylene terephthalate (PET; e.g., Melinex ST507, Dupont deNemours, Wilmington, Del.) substrate and dried in place by passing through convection ovens. General shape and dimensions of the electrode assembly are indicated in FIG. 8B (the sensor is shown as lying flat for clarity; the material was polymer thick film inks on a 0.005 inch thick PET substrate).

The tray and electrode assembly were aligned using precisely punched holes in the sensor substrate that engage with molded-in pins in the tray. The pins were plastically deformed (staked) with a blunt metal punch to fix the sensor substrate to the tray.

Figure 8C:
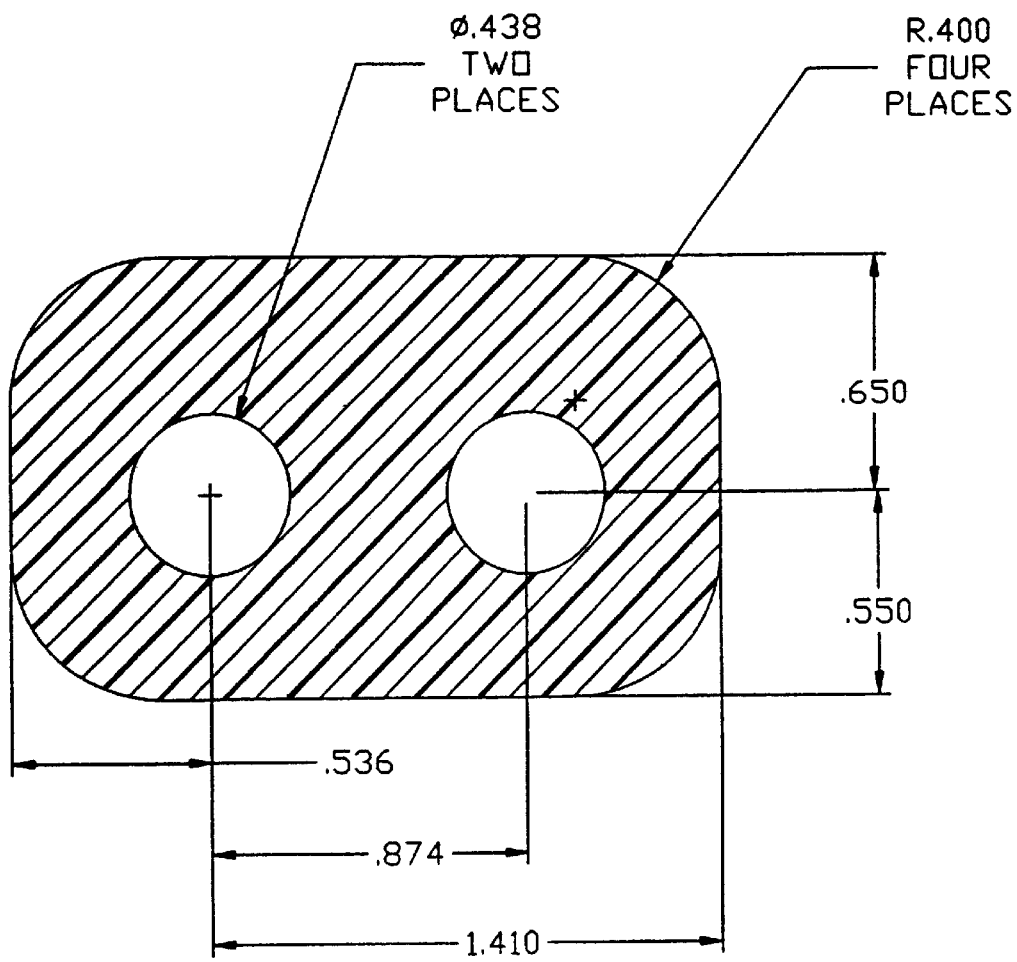
Figure 8D:
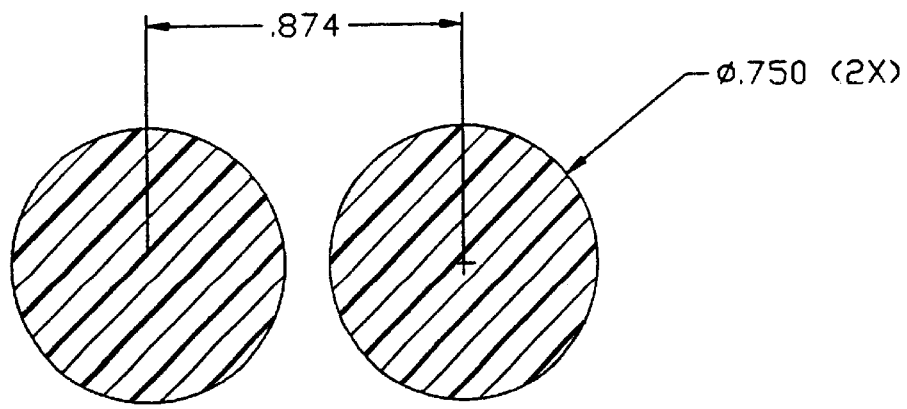
Figure 8E:
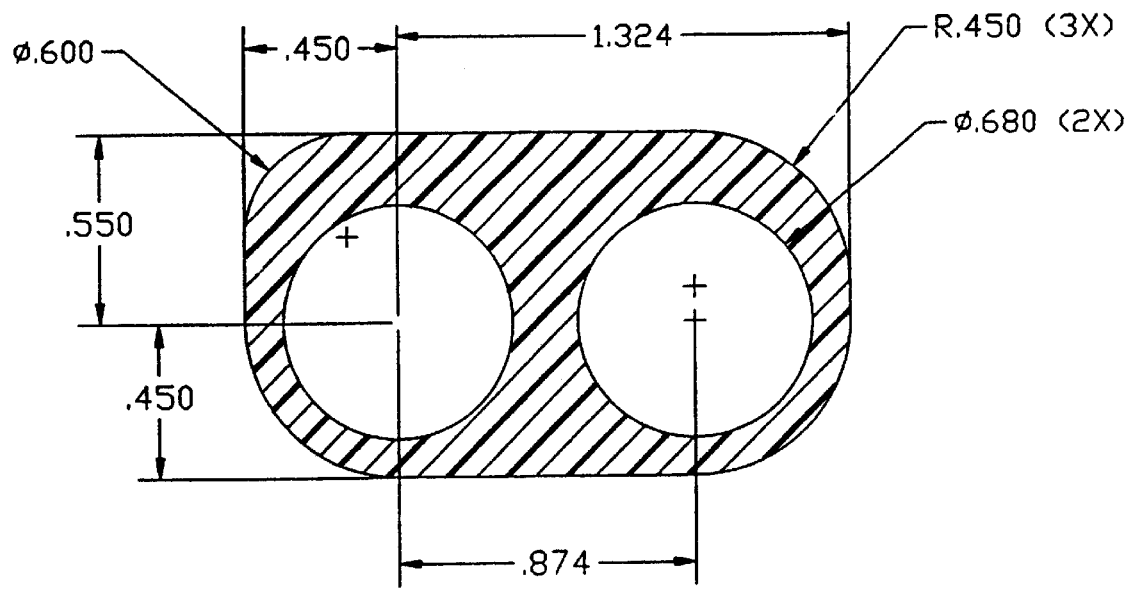

A tri-layer laminate was produced as follows (FIGS. 8C, 8D, and 8E). A mask layer, having the general shape and dimensions shown in FIG. 8C, was produced from a 0.002 inch thick polyurethane film (e.g., Dow Pellethane #2363-80AE; Dow Chemical Corp., Midland, Mich.) coated on one side with an 0.001 inch layer of acrylic pressure sensitive adhesive (e.g., Duro-tak, #87-2196; National Starch and Chemical Corporation, Bridgewater, N.J.). A rotary die cutting press was used to create the circular openings, to create the outline border/perimeter geometry, and to laminate the mask material to the patient liner roll stock (0.003 inch thick PET coated on one side with silicone release; e.g., Fox River #1730 (Fox River Associates, Geneva, Ill.).

The collection inserts were two essentially circular hydrogel disks, illustrated in FIG. 8D, made from a water solution of polyethylene oxide, phosphate buffer, and glucose oxidase, impregnated in a 0.004 inch thick nonwoven PET (e.g., Remay™ #2250). This composite began as roll stock from which circular discs were cut and placed into contact with the mask material using a male-female punch set.

A retaining layer, having the general shape and dimensions shown in FIG. 8E, was produced from 0.001 inch thick PET film (e.g., DuPont Melinex #329; Dupont deNemours, Wilmington, Del.) coated on both sides with a styrene-butadiene-based pressure sensitive adhesive (e.g., RP100; John Deal Corporation, Mount Juliet, Tenn.). A rotary die cutting press was used to create the circular openings and outline border/perimeter geometry. A laminating press was used to place the retaining layer in contact with the collection insert and mask.

The openings in the mask layer were sized to expose a portion of the surface of each collection insert. A border region of the mask layer extended beyond the first surfaces of the collection insert to provide an overhang. The retaining layer was positioned in facing relation with the second surfaces of the collection insert. The retaining layer had two openings which exposes portions of the second surfaces of the collection insert. A border region of the retaining layer extended beyond the second surfaces of the collection insert in order to provide an overhang. The overhanging portions of the mask and retaining layer served as points of attachment where the retaining layer adhesive bound to the non-adhesive surface of the mask and thus prevented movement. This attaching of the layers to each other at their overhanging portions created a laminate where the collection insert was sandwiched between the two layers to provide a three-layer structure.

The mask layer perimeter extended beyond the retaining layer perimeter, thus creating a third overhang. This overhang allows the mask layer to conform to the contours of the biological system to which it is contacted (for example, a human forearm) and to be unencumbered by the rigidity of other parts of the autosensor assembly (for example, the tray and electrodes). Superior adhesion and reduced irritation were achieved by employing such an overhang.

Figure 8F:
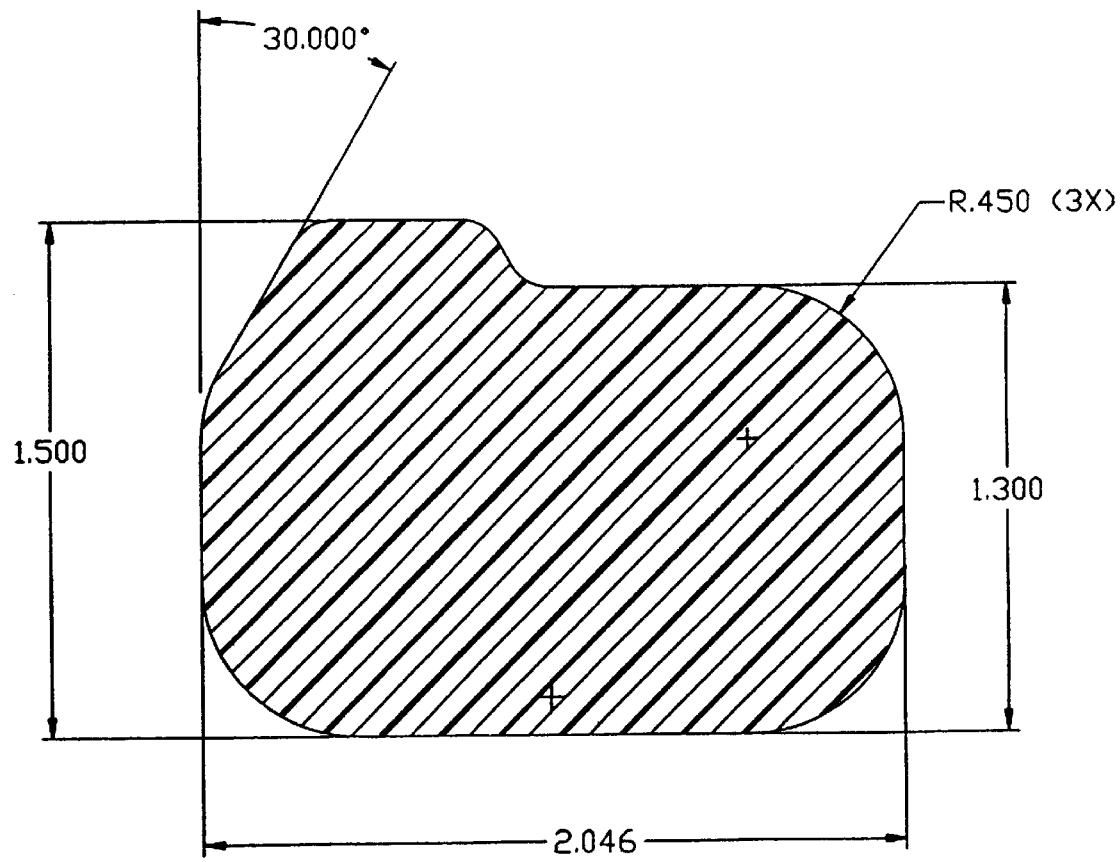
Figure 8G:
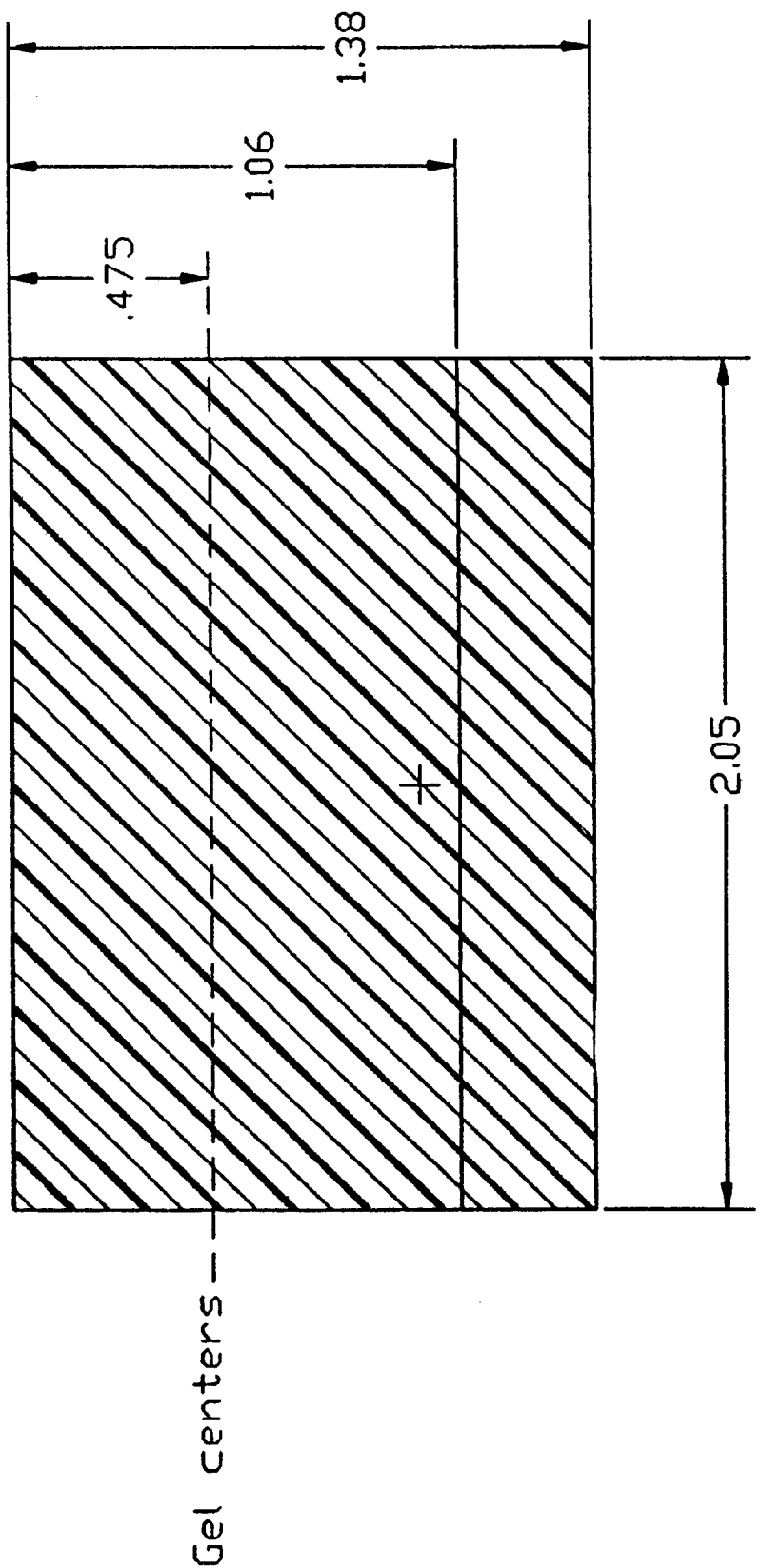
Figure 8H:
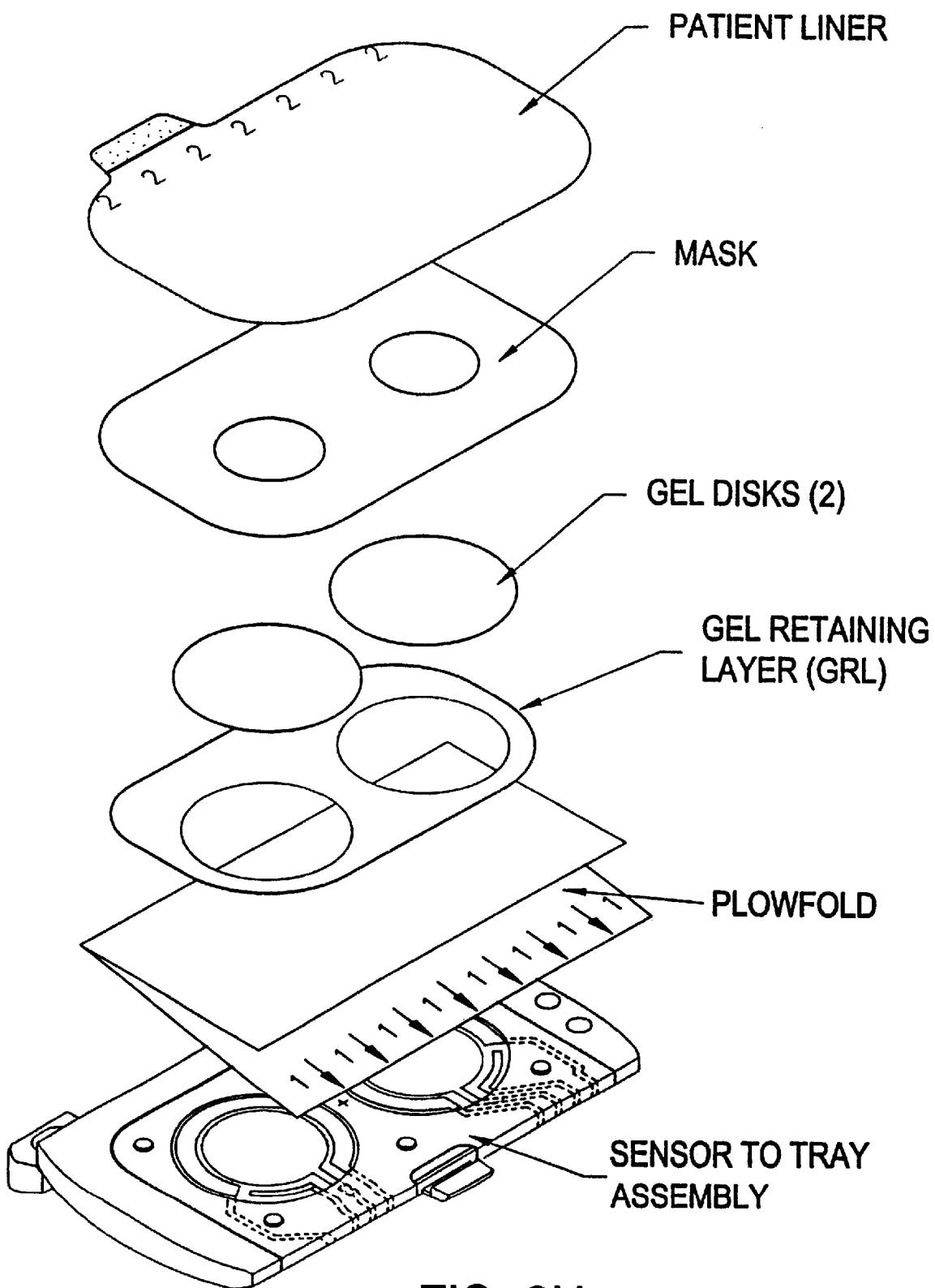

The outline geometry of the patient liner, shown in FIG. 8F, was produced during a blanking operation that used steel rule dies to cut the patient liner roll stock.

A second liner, i.e., a plow-fold liner, for contacting the retaining layer and collection inserts was produced from 0.0016 inch thick biaxially oriented polypropylene film coated on one side with silicone release (e.g., Fox River, #1803; Fox River Associates). The treated side of the plowfold liner faced the collection inserts, retaining layer, and sensor. This film was folded and perforated to length on a rotary press. The folded film was pulled apart at its perforations to create single liners and was laminated to the outer adhesive surface of the retaining layer (dimensions shown in FIG. 8G).

The plowfold liner, as described, left a portion of the retaining layer adhesive exposed. This adhesive was pressed into contact with the electrode-to-tray assembly during the plowfold lamination process, thus adhering the tri-layer laminate with liners to the electrode-to-tray assembly. A custom-designed assembly machine performed the lamination using fixtures to precisely align the components relative to each other. Each component part nested precisely within its respective fixture to provide the necessary alignment. Vacuum was used to keep the parts from falling out of their fixtures during assembly.

The entire assembly described above (FIG. 8H), including, the tray, electrode assembly, tri-layer laminate, and liners, comprises an exemplary autosensor assembly of the present invention.

This particular embodiment of the autosensor assembly is also graphically represented in FIG. 3 and FIGS. 8A–8H and is intended for use in the Glucowatch® biographer (Cygnus, Inc., Redwood City, Calif.), an iontophoretic sampling system for glucose concentration monitoring of a subject.

Alternative materials for the components described above include, but are not limited to, the following:

(i) Alternate Mask, Retaining Layer, Patient Liner, and Plowfold Liner Materials: high density polyethylene (HDPE), low density polyethylene (LDPE), very low density polyethylene (VLDPE), polyethylene copolymers, thermoplastic elastomers, silicon elastomers, polyurethane (PU), polypropylene (PP), (PET), nylon, flexible polyvinylchloride (PVC), natural rubber, synthetic rubber, and suitable combinations of the foregoing materials.

(ii) Base films: polyurethane, polyethylene (high density, medium density, low density, very low density, linear low density, very low density linear), polyethylene terephthalate (PET, polyester), vinyl, polystyrene, polycarbonate, diacetate, paper products, blends of these materials, foam films made from any of the same materials;

(iii) Adhesives: acrylic based pressure-sensitive, rubber based pressure-sensitive (for example, styrene butadiene rubber (SBR) based adhesives, styrene-ethylene-butylene rubber (SEBR) based adhesives), cyanoacrylates, epoxies, acrylate, and other pressure sensitive adhesives.

(iv) Release coatings: silicone, florinated polymers, chlorinated polymers; and (v) Alternate tray materials: polycarbonate; PETG (polyethylene terephthalate copolymer); ABS (acrylonitrile-butadiene-styrene co-polymer); SAN (styrene-acrylonitrile copolymer); SMA (styrene-maleic anhydride copolymer); HIPS (high impact polystryrene); polyethylene terephthalate (PET); polystyrene (PS); polypropylene (PP); and blends thereof.

Example 2

Another Embodiment of the Autosensor Assembly

Figure 9A:
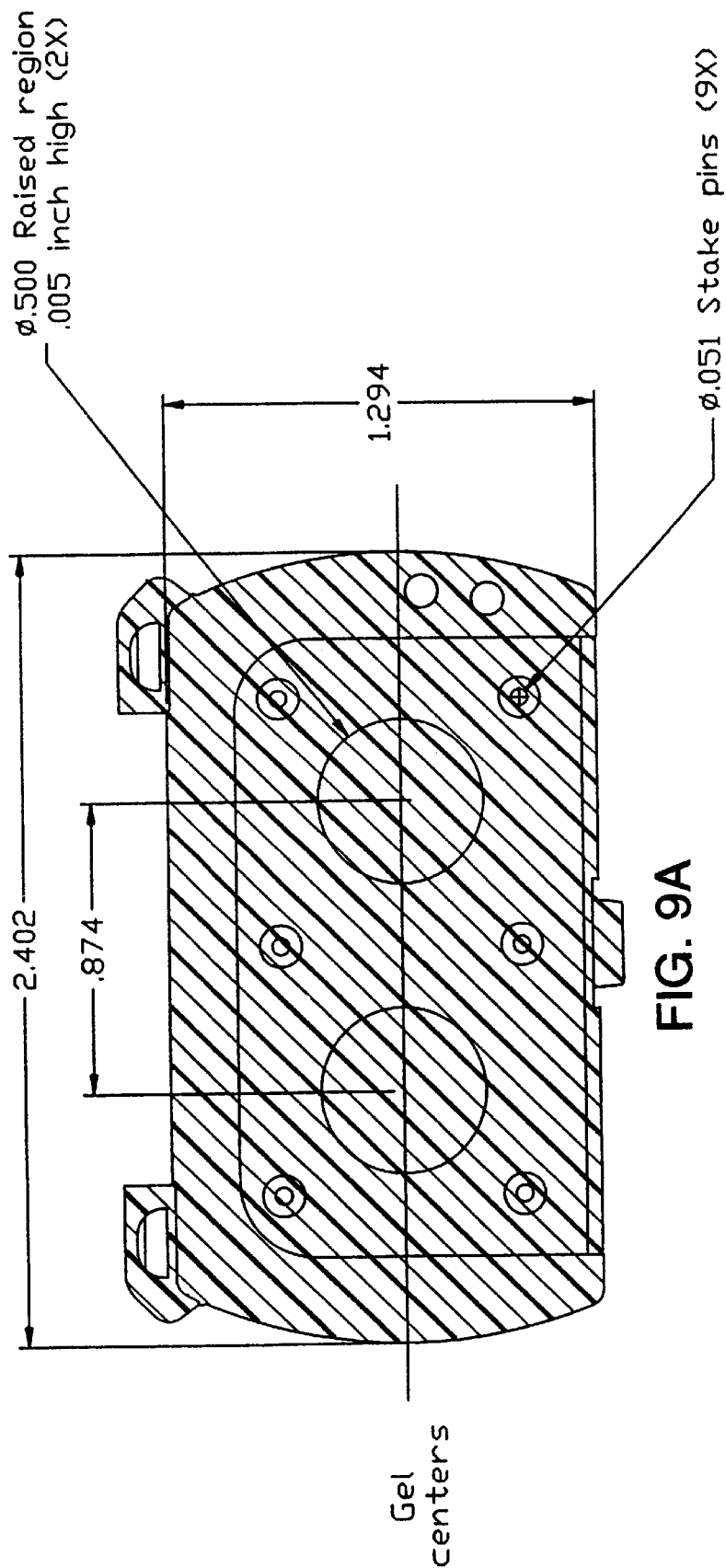
FIGS. 9A through 9G show general schematic diagrams for the components of another embodiment of an autosensor of the present invention. The general shape and dimensions of the tray are indicated in FIG. 9A. General shape and dimensions of the electrode assembly are indicated in FIG. 9B. A mask layer is shown, having the general shape and dimensions shown in FIG. 9C. The general shape and dimensions of collection inserts are shown in FIG. 9D.

A tray is produced using a high impact polystyrene (e.g., Chevron HG200N02) in a plastic injection molding process. General shape and dimensions of the tray are indicated in FIG. 9A (the tray was 0.110 inches thick, with raised areas indicated in the figure). Dimensions in all FIGS. 9A to 9G are given in inches.

Sensor-to-tray is assembled as described in Example 1. All other components are made by cutting from sheet stock using still rule dies, and hand assembled using visual alignment.

Figure 9B:
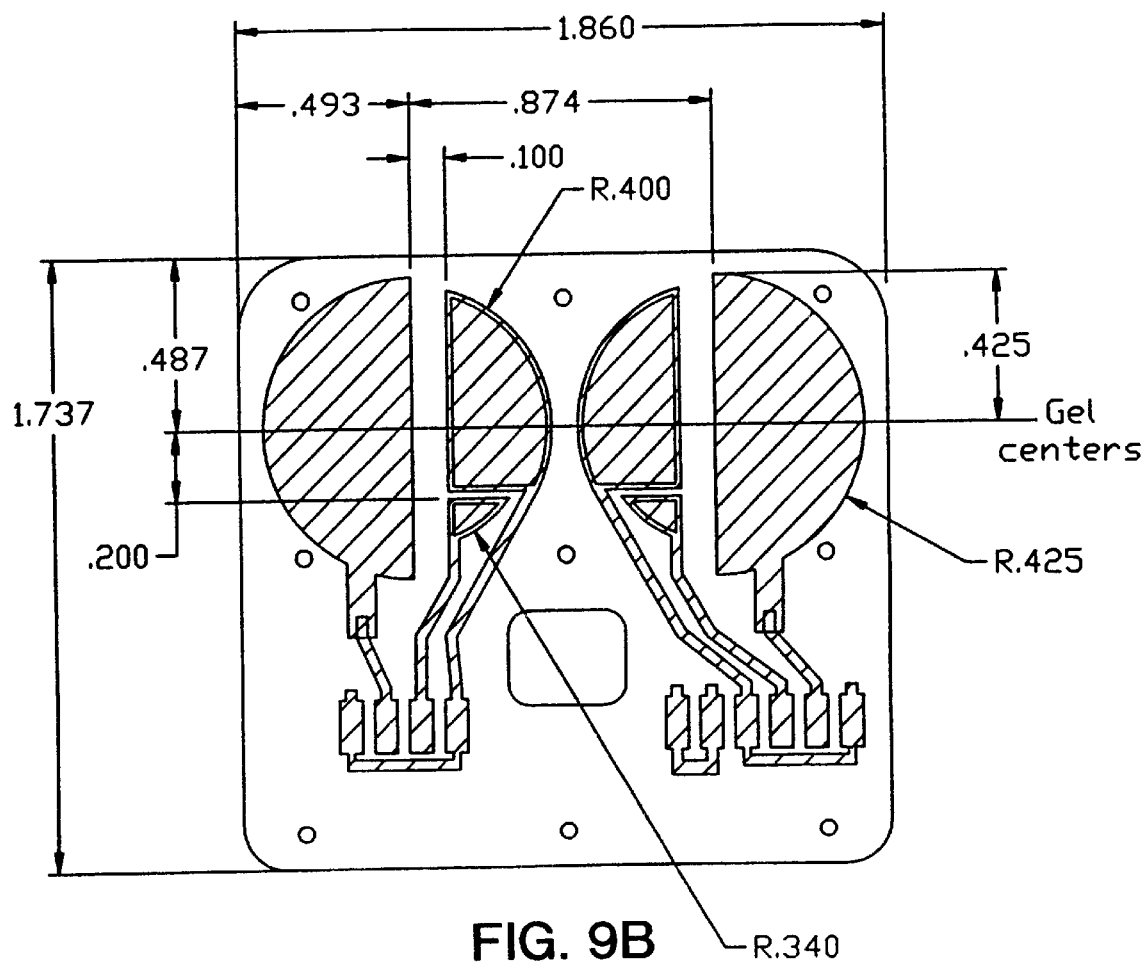

An electrode assembly is produced using thick film ink formulations in a screen printing process. Each ink formulation comprises: a) an electrically conductive particulate b) an electrochemically active particulate, c) a polymeric binder, and d) a volatile organic solvent to create a liquid slurry. During screen printing, the inks are patterned onto the polyethylene terephthalate (PET) substrate and dried in place by passing through convection ovens. General shape and dimensions of the electrode assembly are indicated in FIG. 9B (the sensor is shown as lying flat for clarity; the material is polymer thick film inks on a 0.005 inch thick PET substrate).

The tray and electrode assembly are aligned using precisely punched holes in the sensor substrate that engage with molded-in pins in the tray. The pins are plastically deformed (staked) with a blunt metal punch to fix the sensor substrate to the tray.

Figure 9C:
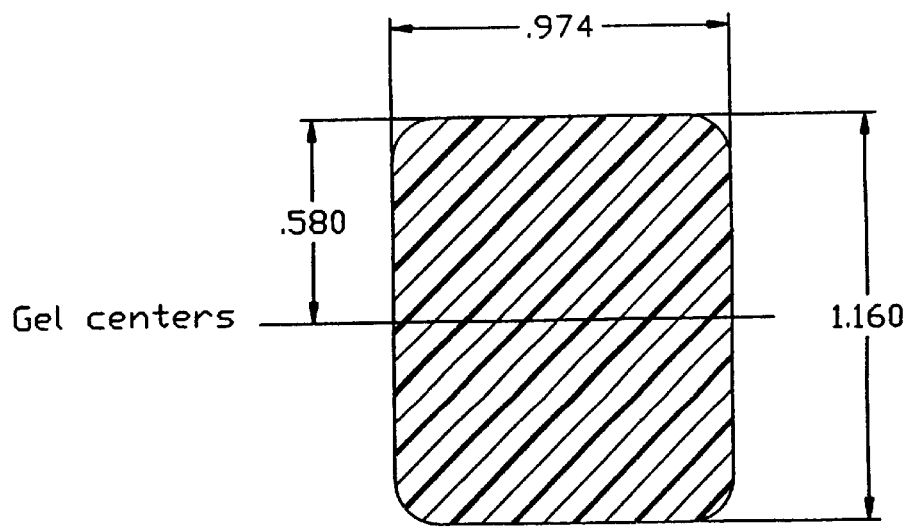

A mask layer having the general shape and dimensions shown in FIG. 9C is produced (steel-rule die cut from sheet stock) from 0.0015 inch Deerfield natural HDPE coated on two side with 0.001 inch adhesive (e.g., Duro-tak™, #87-2196; National Starch and Chemical Corporation, Bridgewater, N.J.).

Figure 9D:
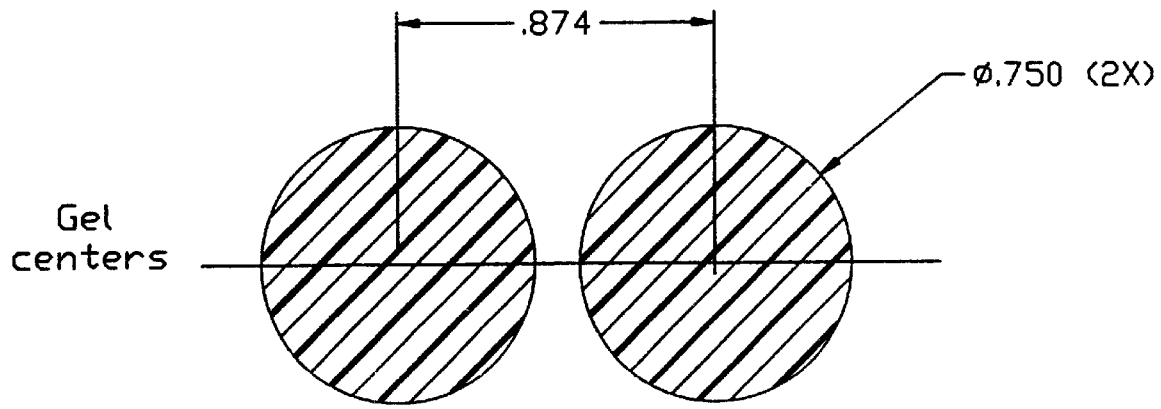

The collection inserts are two essentially circular hydrogel disks, illustrated in FIG. 9D, made from a water solution of polyethylene oxide, phosphate buffer, and glucose oxidase, impregnated in a 0.004 inch thick nonwoven PET (e.g., Remay™ #2250). This composite begins as roll stock from which circular discs are steel-rule die cut.

Figure 9E:
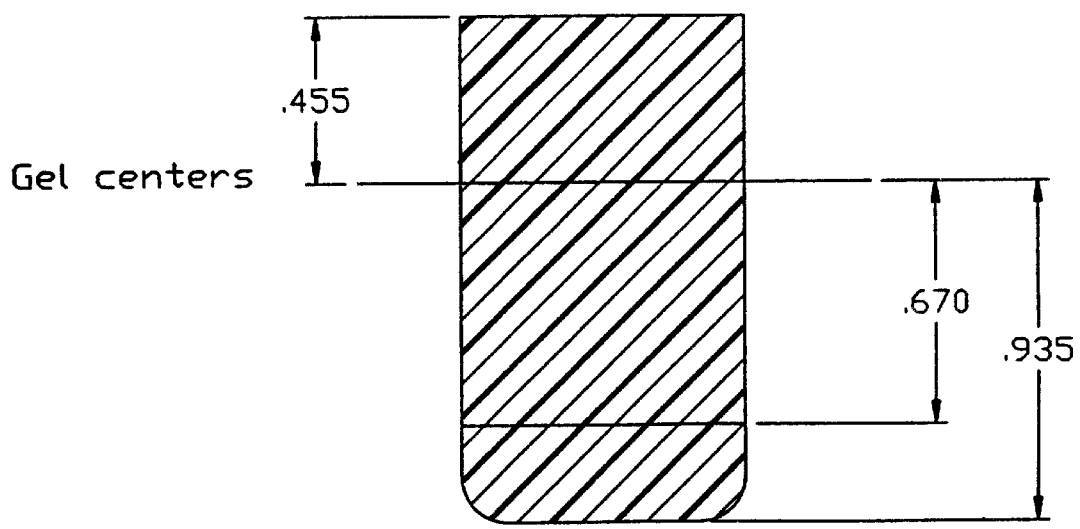

A plowfold liner having the general shape and dimensions shown in FIG. 9E is produced from 0.0016 inch thick biaxially oriented polypropylene film coated on one side with silicone release (e.g., Fox River, #1803; Fox River Associates). This film is folded and perforated to length on a rotary press. The folded film is pulled apart at its perforations to create single liners and is laminated to the outer adhesive surface of the retaining layer.

Figure 9F:
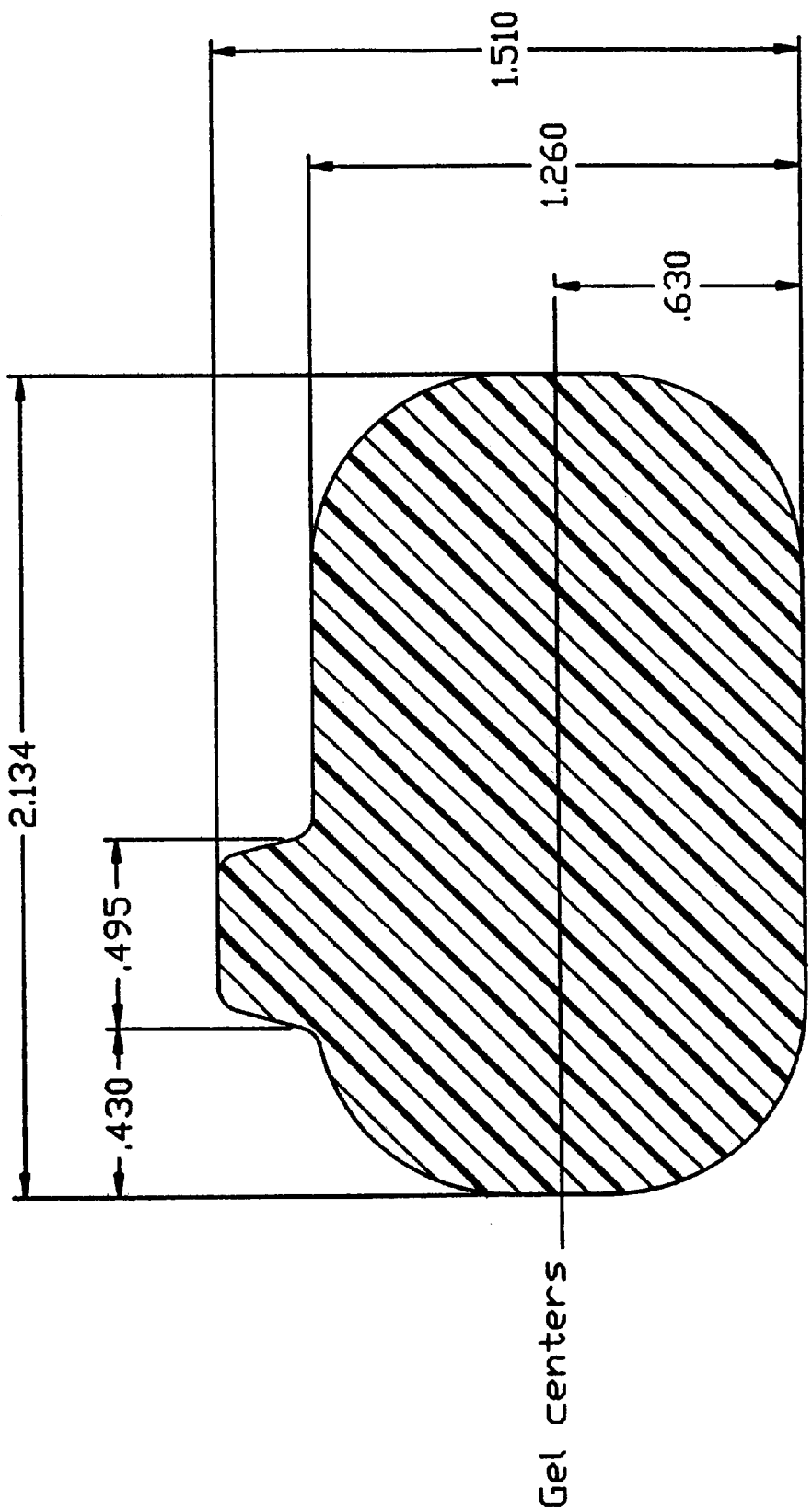

A patient liner having the general shape and dimensions shown in FIG. 9F is produced (steel-rule die cut from sheet stock) from, for example, 0.003 inch Fox River (#1806) PET coated on one side (facing/contacting the mask) with silicone release.

The components are assembled in the following order from the bottom up (for example, using manual assembly and human visual alignment): (1) sensor-to-tray assembly; (2) plowfold liner; (3) gel disks (collection inserts); (4) mask layer; and (5) patient liner.

Figure 9G:
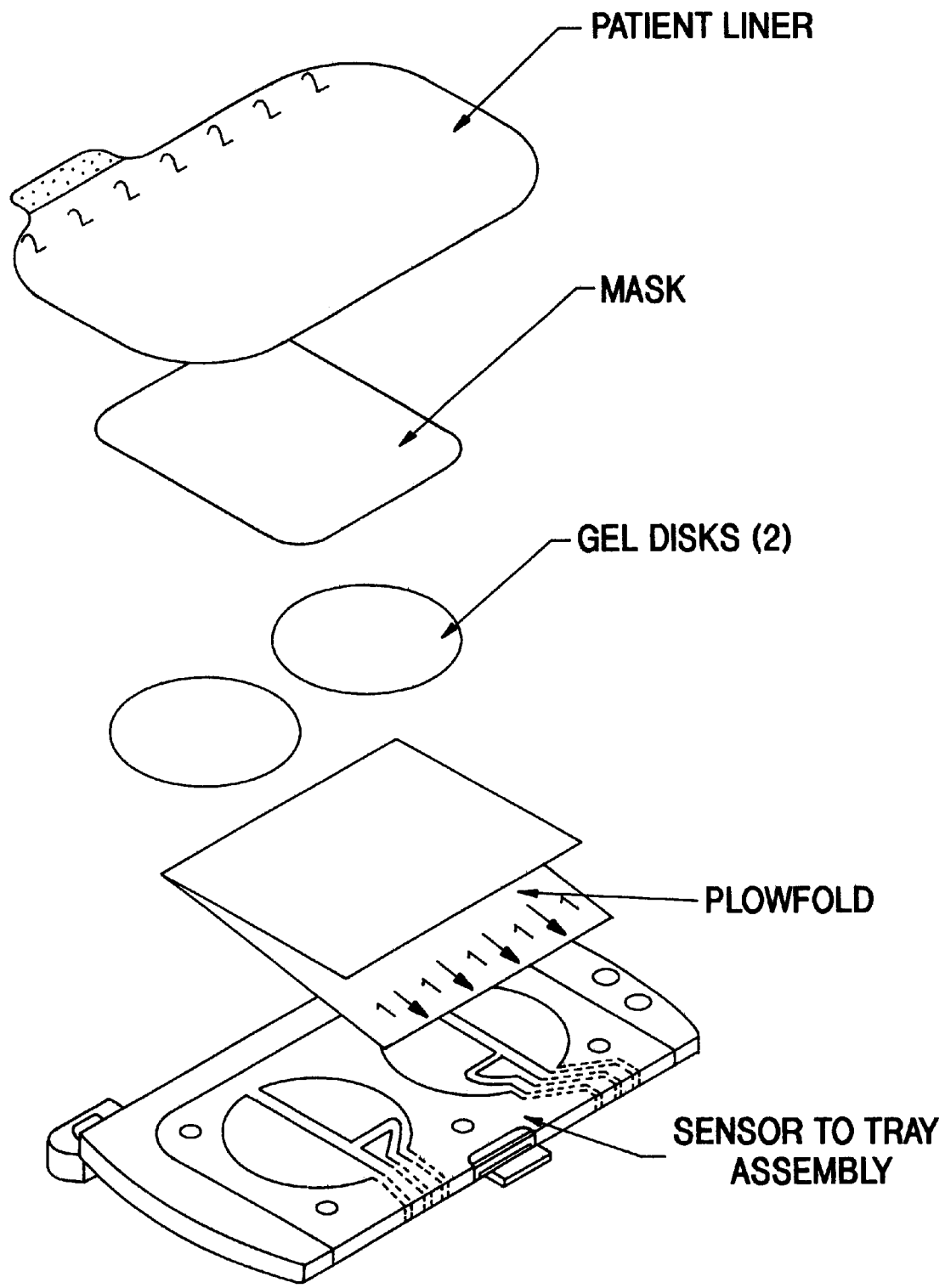

FIG. 9G shows a plan view of the assembly just described with all components showing.

Accordingly, novel laminates, collection assemblies, and autosensor assemblies are disclosed. Although preferred embodiments of the subject invention have been described in some detail, it is understood that obvious variations can be made without departing from the spirit and the scope of the invention as defined by the appended claims.

What is claimed is:

1. A method of producing a collection assembly, for use in an iontophoretic sampling device useful to monitor a selected analyte or derivatives thereof present in a biological system, said method comprising:

providing (a) first and second collection inserts each insert comprising an ionically conductive material having first and second surfaces;

(b) a mask comprising (i) a material that is substantially impermeable to the selected analyte or derivatives thereof, and (ii) inner and outer faces, wherein said mask defines first and second openings and a border; and (c) a retaining layer, comprising inner and outer faces, wherein said retaining layer defines first and second openings and a border; and positioning (a) the inner face of the mask in facing relation with the first surface of each collection insert, such that (i) said first and second openings of the mask are, respectively, aligned with the first and second collection inserts (ii) each opening of the mask exposes at least a portion of the first surface of the collection insert with which it is aligned, and (iii) said border extends beyond the first surface of each of the collection inserts to provide an overhang; and (b) the inner face of the retaining layer in facing relation with the second surface of each collection insert, such that (i) said first and second openings of the retaining layer are, respectively, aligned with the first and second collection inserts, (ii) each opening of the retaining layer exposes at least a portion of the second surface of the collection insert with which it is aligned, and (iii) said border extends beyond the first surface of each of the collection inserts to provide an overhang, thereby resulting in production of said collection assembly.

2. The method of claim 1, wherein the inner face of the mask contacts the inner face of the retaining layer, and the overhang provided by the mask and the overhang provided by the retaining layer sandwich the collection inserts therebetween.

3. The method of claim 2, wherein the border of said mask defines a perimeter and the border of the retaining layer defines a perimeter, and the perimeter of the mask is greater than the perimeter of the retaining layer thus forming an overhang of the mask relative to the perimeter of the retaining layer.

4. The method of claim 1, wherein the mask is comprised of a material selected from the group consisting of high density polyethylene (HDPE), low density polyethylene (LDPE), very low density polyethylene (VLDPE), polyethylene copolymers, thermoplastic elastomers, silicon elastomers, polyurethane (PU), polypropylene (PP), (PET), nylon, flexible polyvinylchloride (PVC), natural rubber, synthetic rubber, and combinations thereof.

5. The method of claim 1, wherein the retaining layer is comprised of a material selected from the group consisting of high density polyethylene (HDPE), low density polyethylene (LDPE), very low density polyethylene (VLDPE), polyethylene copolymers, thermoplastic elastomers, silicon elastomers, polyurethane (PU), polypropylene (PP), (PET), nylon, flexible polyvinylchloride (PVC), natural rubber, synthetic rubber, and combinations thereof.

6. The method of claim 1, wherein at least one of the collection inserts comprises an enzyme.

7. The method of claim 6, wherein at least one of the collection inserts comprises glucose oxidase.

8. The method of claim 7, wherein both collection inserts comprise glucose oxidase.

9. The method of claim 1, wherein each collection insert comprises a hydrogel.

10. The method of claim 1, wherein the outer face of the retaining layer comprises an adhesive.

11. The method of claim 1, wherein before positioning said retaining layer and said collection inserts the outer face of the retaining layer is contacted with a first surface of a first removable liner.

12. The method of claim 11, wherein said first removable liner has a plow-fold shape.

13. The method of claim 1, wherein before positioning said mask and said collection inserts the outer face of the mask is contacted with a first surface of a second removable liner.

14. The method of claim 1, further comprising attaching a first removable liner to the outer face of the retaining layer, and a second removable liner to the outer face of the mask.

15. The method of claim 1, wherein the outer face of the mask comprises an adhesive.

16. The method of claim 1, wherein said positioning farther comprises aligning the first and second openings in the mask with the first and second openings in the retaining layer.

17. The method of claim 1, wherein after positioning the mask, retaining layer, and collection inserts, the mask and retaining layers are contacted along a central portion, wherein said central portion separates the first and second openings in each layer such that said first and second collection inserts are separately sandwiched between the mask and retaining layers.

18. The method of claim 1, wherein said analyte is glucose.

19. The method of claim 1, wherein after positioning the mask, retaining layer, and collection inserts, the mask is bonded to the retaining layer, thereby producing a laminate of the collection assembly.

20. The method of claim 1, further comprising packaging the collection assembly and sealing the package, thereby producing a packaged collection assembly.

21. The method of claim 19, further comprising packaging the collection assembly and sealing the package, thereby producing a packaged collection assembly.

22. The method of claim 20, further comprising adding a hydrating insert to the package before sealing.

23. The method of claim 1, wherein at least one of the collection inserts comprises an enzyme.

24. The method of claim 23, wherein at least one of the collection inserts comprises glucose oxidase.

25. The method of claim 24, wherein both collection inserts comprise glucose oxidase.

26. A method of producing an autosensor assembly, for use in an iontophoretic sampling device useful to monitor a selected analyte or derivatives thereof present in a biological system, said method comprising:

providing (a) first and second collection inserts each insert comprising an ionically conductive material having first and second surfaces;

(b) a mask comprising (i) a substantially planar material that is substantially impermeable to the selected analyte or derivatives thereof, and (ii) inner and outer faces, wherein said mask defines first and second openings and a border;

(c) a retaining layer, comprising inner and outer faces, wherein said retaining layer defines first and second openings and a border;

(d) first and second electrode assemblies, each electrode assembly comprising (i) first and second surfaces, and (ii) said first surface comprising an electrode; and (e) a support tray; and positioning (a) the inner face of the mask in facing relation with the first surface of each collection insert, such that (i) said first and second openings of the mask are, respectively, aligned with the first and second collection inserts, (ii) each opening of the mask exposes at least a portion of the first surface of the collection insert with which it is aligned, and (iii) said border extends beyond the first surface of each of the collection inserts to provide an overhang;

(b) the inner face of the retaining layer in facing relation with the second surface of each collection insert, such that (i) said first and second openings of the retaining layer are, respectively, aligned with the first and second collection inserts, (ii) each opening of the retaining layer exposes at least a portion of the second surface of the collection insert with which it is aligned, and (iii) said border extends beyond the first surface of each of the collection inserts to provide an overhang;

(c) said first and second electrode assemblies relative to the outer face of the retaining layer such that a first surface of the electrode of the first electrode assembly is aligned with the first opening in the retaining layer, and a first surface of the electrode of the second electrode assembly is aligned with the second opening in the retaining layer; and (d) said support tray such that it contacts the second surface of each electrode assembly, thereby resulting in production of said autosensor assembly.

27. The method of claim 26, wherein the inner face of the mask contacts the inner face of the retaining layer, and the overhang provided by the mask and the overhang provided by the retaining layer sandwich the collection inserts therebetween.

28. The method of claim 27, wherein the border of said mask defines a perimeter and the border of the retaining layer defines a perimeter, and the perimeter of the mask is greater than the perimeter of the retaining layer thus forming an overhang of the mask relative to the perimeter of the retaining layer.

29. The method of claim 27, wherein after positioning the mask, retaining layer, and collection inserts, the mask and retaining layers are contacted along a central portion, wherein said central portion separates the first and second openings in each layer such that said first and second collection inserts are separately sandwiched between the mask and retaining layers.

30. The method of claim 26, wherein the mask is comprised of a material selected from the group consisting of high density polyethylene (HDPE), low density polyethylene (LDPE), very low density polyethylene (VLDPE), polyethylene copolymers, thermoplastic elastomers, silicon elastomers, polyurethane (PU), polypropylene (PP), (PET), nylon, flexible polyvinylchloride (PVC), natural rubber, synthetic rubber, and combinations thereof.

31. The method of claim 26, wherein the retaining layer is comprised of a material selected from the group consisting of high density polyethylene (HDPE), low density polyethylene (LDPE), very low density polyethylene (VLDPE), polyethylene copolymers, thermoplastic elastomers, silicon elastomers, polyurethane (PU), polypropylene (PP), (PET), nylon, flexible polyvinylchloride (PVC), natural rubber, synthetic rubber, and combinations thereof.

32. The method of claim 26, wherein each collection insert comprises a hydrogel.

33. The method of claim 26, wherein the outer face of the retaining layer comprises an adhesive.

34. The method of claim 26, wherein before positioning said retaining layer and said collection inserts the outer face of the retaining layer is contacted with a first surface of a first removable liner.

35. The method of claim 34, wherein said first removable liner has a plow-fold shape.

36. The method of claim 26, wherein before positioning said mask and said collection inserts the outer face of the mask is contacted with a first surface of a second removable liner.

37. The method of claim 26, wherein before said positioning a first removable liner is attached to the outer face of the retaining layer, and a second removable liner is attached to the outer face of the mask.

38. The method of claim 26, wherein the outer face of the mask comprises an adhesive.

39. The method of claim 26, wherein said positioning further comprises aligning the first and second openings in the mask with the first and second openings in the retaining layer.

40. The method of claim 26, wherein after positioning the mask, retaining layer, and collection inserts, the mask and retaining layers are contacted along a central portion, wherein said central portion separates the first and second openings in each layer such that said first and second collection inserts are separately sandwiched between the mask and retaining layers.

41. The method of claim 26, wherein the electrode of each electrode assembly comprises a bimodal electrode.

42. The method of claim 41, wherein each electrode assembly further comprises a sensing electrode.

43. The method of claim 42, wherein each electrode assembly further comprises a reference electrode.

44. The method of claim 26, wherein said analyte is glucose.

45. The method of claim 26, wherein after positioning the mask, retaining layer, and collection inserts, the mask is bonded to the retaining layer, thereby producing a laminate of the collection assembly.

46. The method of claim 26, further comprising packaging the autosensor assembly and sealing the package, thereby producing a packaged autosensor assembly.

47. The method of claim 45, further comprising packaging the autosensor assembly and sealing the package, thereby producing a packaged autosensor assembly.

48. The method of claim 46, further comprising adding a hydrating insert to the package before sealing.

49. A method of producing an autosensor assembly, for use in an iontophoretic sampling device useful to monitor glucose present in a biological system, said method comprising:
   providing (a) first and second collection inserts each insert comprising a hydrogel, each hydrogel comprising, (i) an ionically conductive material having first and second surfaces, and (ii) glucose oxidase;
   (b) a mask comprising (i) a substantially planar material that is substantially impermeable to the selected analyte or derivatives thereof, and (ii) inner and outer faces, wherein said mask defines first and second openings and a border;
   (c) a retaining layer, comprising inner and outer faces, wherein said retaining layer defines first and second openings and a border;
   (d) first and second electrode assemblies, each electrode assembly comprising (i) first and second surfaces, and (ii) said first surface comprising a bimodal electrode, a reference electrode, and a sensing electrode; and
   (e) a support tray; and
   positioning (a) the inner face of the mask in facing relation with the first surface of each collection insert, such that (i) said first and second openings of the mask are, respectively, aligned with the first and second collection inserts, (ii) each opening of the mask exposes at least a portion of the first surface of the collection insert with which it is aligned, and (iii) said border extends beyond the first surface of each of the collection inserts to provide an overhang; and
   (b) the inner face of the retaining layer in facing relation with the second surface of each collection insert, such that (i) said first and second openings of the retaining layer are, respectively, aligned with the first and second collection inserts, (ii) each opening of the retaining layer exposes at least a portion of the second surface of the collection insert with which it is aligned, and (iii) said border extends beyond the first surface of each of the collection inserts to provide an overhang;
   (c) said first and second electrode assemblies relative to the outer face of the retaining layer such that the bimodal electrode, reference electrode, and sensing electrode, of the first electrode assembly are aligned with the first opening in the retaining layer, and the bimodal electrode, reference electrode, and sensing electrode of the second electrode assembly is aligned with the second opening in the retaining layer, and
   (d) said support tray such that it contacts the second surface of each electrode assembly, thereby resulting in production of said autosensor assembly.

50. The method of claim 49, wherein the inner face of the mask contacts the inner face of the retaining layer, and the overhang provided by the mask and the overhang provided by the retaining layer sandwich the collection inserts therebetween.

51. The method of claim 50, wherein the border of said mask defines a perimeter and the border of the retaining layer defines a perimeter, and the perimeter of the mask is greater than the perimeter of the retaining layer thus forming an overhang of the mask relative to the perimeter of the retaining layer.

52. The method of claim 51, wherein after positioning the mask, retaining layer, and collection inserts, the mask is bonded to the retaining layer, thereby producing a laminate of the collection assembly.

53. The method of claim 52, wherein the mask is comprised of a material selected from the group consisting of high density polyethylene (HDPE), low density polyethylene (LDPE), very low density polyethylene (VLDPE), polyethylene copolymers, thermoplastic elastomers, silicon elastomers, polyurethane (PU), polypropylene (PP), (PET), nylon, flexible polyvinylchloride (PVC), natural rubber, synthetic rubber, and combinations thereof.

54. The method of claim 52, wherein the retaining layer is comprised of a material selected from the group consisting of high density polyethylene (HDPE), low density polyethylene (LDPE), very low density polyethylene (VLDPE), polyethylene copolymers, thermoplastic elastomers, silicon elastomers, polyurethane (PU), polypropylene (PP), (PET), nylon, flexible polyvinylchloride (PVC), natural rubber, synthetic rubber, and combinations thereof.

55. The method of claim 52, wherein before positioning said retaining layer and said collection inserts the outer face of the retaining layer is contacted with a first surface of a first removable liner.

56. The method of claim 55, wherein said first removable liner has a plow-fold shape.

57. The method of claim 56, wherein before positioning said mask and said collection inserts the outer face of the mask is contacted with a first surface of a second removable liner.

58. The method of claim 57, further comprising packaging the autosensor assembly and sealing the package, thereby producing a packaged autosensor assembly.

59. The method of claim 58, further comprising adding a hydrating insert to the package before sealing.

* * * * *

UNITED STATES PATENT AND TRADEMARK OFFICE
CERTIFICATE OF CORRECTION

PATENT NO. : 6,341,232 B1
DATED : January 22, 2002
INVENTOR(S) : Thomas E. Conn et al.

It is certified that error appears in the above-identified patent and that said Letters Patent is hereby corrected as shown below:

<u>Title page,</u>
Related U.S. Application Data, "[60] Provisional application No. 60/085,345, filed on May 13, 1999" should be -- [60] Provisional application No. 60/085,345, filed on May 13, 1998 --.

Signed and Sealed this

Fourth Day of June, 2002

*Attest:*

*Attesting Officer*

JAMES E. ROGAN
*Director of the United States Patent and Trademark Office*

Disclaimer 6,341,232 B1 — Thomas E. Conn, Palo Alto, CA; Russell Ford, San Francisco, CA; Pravin L. Soni, Sunnyvale, CA; Michael J. Tierney, San Jose, CA; Prema Vijayakumar, Fremont, CA. METHODS OF PRODUCING COLLECTION ASSEMBLIES, LAMINATES, AND AUTOSENSOR ASSEMBLIES FOR USE IN TRANSDERMAL SAMPLING SYSTEMS. Patented January 22, 2002. Disclaimer filed April 16, 2004, by the assignee, Cygnus, Inc.

The term of this patent shall not extend beyond the expiration date of Patent No. 6,341,232.

*(Official Gazette, September 21, 2004)*